United States Patent [19]

Bailey et al.

[11] Patent Number: 5,055,458

[45] Date of Patent: Oct. 8, 1991

[54] PURINE DERIVATIVES HAVING ANTIVIRAL ACTIVITY

[75] Inventors: Stuart Bailey; Michael R. Harnden, both of Epsom, England

[73] Assignee: Beecham Group P.l.c., Brentford, England

[21] Appl. No.: 387,068

[22] Filed: Jul. 28, 1989

[30] Foreign Application Priority Data

Aug. 2, 1988 [GB] United Kingdom ............... 8818375
Nov. 28, 1988 [GB] United Kingdom ............... 8827724

[51] Int. Cl.[5] .................. A61K 31/675; A61K 31/52; C07F 9/6561
[52] U.S. Cl. .................................... 514/81; 544/244; 544/243; 548/112; 556/404; 558/175
[58] Field of Search ........................... 544/244; 514/81

[56] References Cited

U.S. PATENT DOCUMENTS 4,724,233 2/1988 De Clercq et al. .................. 514/81
4,808,716 2/1989 Hol et al. ............................ 544/244
4,910,307 3/1990 Wyatt .................................. 544/276

FOREIGN PATENT DOCUMENTS 0242482 10/1987 European Pat. Off.
0294069 12/1988 European Pat. Off. ............ 544/277
0298601 1/1989 European Pat. Off. ............ 544/277
0319228 6/1989 European Pat. Off. ............ 544/244

OTHER PUBLICATIONS

Prisbe, et al., J. Med. Chem., vol. 29(5), pp. 671–675 (05/86).
Duke, et al., Antiviral Research, vol. 6, pp. 299–308 (1986).
Streicher, et al., Chemica Scripta, vol. 26, pp. 179–183 (1986).
Holy, et al., Collection Czechoslosovak Chem. Commun., vol. 52(9) pp. 2775–2791 (09/87).
Watson, et al., J. Org. Chem., vol. 39(19), pp. 2911–2916 (09/74).
Bronson et al., "Nucleotide Analogues as Antiviral Agents", ed. Martin, American Chemical Society, (1989), pp. 71–87.
Holy, et al., "Nucleotide Analogues As Antiviral Agents", Martin Ed., American Chemical Society, (1989), pp. 61–71.

Primary Examiner—Diana Rivers
Attorney, Agent, or Firm—Hopgood, Calimafde, Kalil, Blaustein & Judlowe

[57] ABSTRACT

Compounds of formula (I) and pharmaceutically acceptable salts thereof:

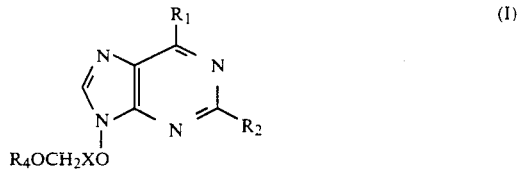

wherein
$R_1$ is hydroxy, amino, chloro or $OR_7$ wherein
$R_7$ is $C_{1-6}$ alkyl, phenyl or phenyl $C_{1-2}$ alkyl either of which phenyl moieties may be substituted by one or two substituents selected from halo, $C_{1-4}$ alkyl or $C_{1-4}$ alkoxy;
$R_2$ amino or, when $R_1$ is hydroxy or amino, $R_2$ may also be hydrogen;
X is —CH$_2$CH$_2$— or a moiety of structure (a), (b) or (c):

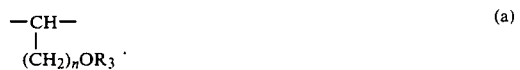

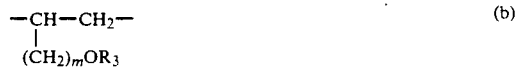

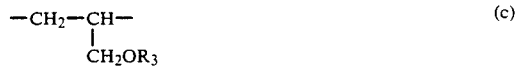

wherein
n is 1 or 2;
m is 0, 1 or 2; and
$R_3$ is hydrogen or acyl;
$R_4$ is a group of formula:

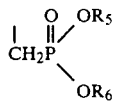

wherein
$R_5$ and $R_6$ are independently selected from hydrogen, $C_{1-6}$ alkyl and optionally substituted phenyl; having antiviral activity, processes for their preparation and their use as pharmaceuticals.

10 Claims, No Drawings

PURINE DERIVATIVES HAVING ANTIVIRAL ACTIVITY

The present invention relates to compounds having antiviral activity, to processes for their preparation and to their use as pharmaceuticals.

EP-A-242482 (Beecham Group p.l.c.) describes a group of guanine derivatives having a 9-hydroxyalkoxy substituent, and possessing antiviral activity.

A novel, structurally distinct class of compounds has now been discovered, these compounds also having antiviral activity.

Accordingly, the present invention provides a compound of formula (I), or a pharmaceutically acceptable salt thereof:

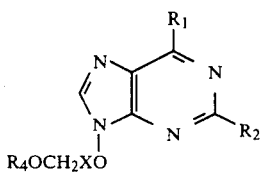

wherein
$R_1$ is hydroxy, amino, chloro or $OR_7$ wherein
$R_7$ is $C_{1-6}$ alkyl, phenyl or phenyl $C_{1-2}$ alkyl either of which phenyl moieties may be substituted by one or two substituents selected from halo, $C_{1-4}$ alkyl or $C_{1-4}$ alkoxy;
$R_2$ is amino or, when $R_1$ is hydroxy or amino, $R_2$ may also be hydrogen;
X is —$CH_2CH_2$— or a moiety of structure (a), (b) or (c):

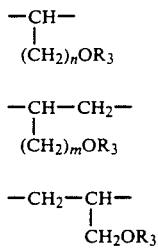

wherein
n is 1 or 2;
m is 0, 1 or 2; and
$R_3$ is hydrogen or acyl;
$R_4$ is a group of formula:

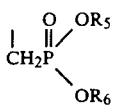

wherein
$R_5$ and $R_6$ are independently selected from hydrogen, $C_{1-6}$ alkyl and optionally substituted phenyl.

When $R_1$ is hydroxy and $R_2$ is amino, the compound of formula (I) is a guanine derivative;
When $R_1$ is amino and $R_2$ is hydrogen, the compound of formula (I) is an adenine derivative;
When $R_1$ is hydroxy and $R_2$ is hydrogen, the compound of formula (I) is a hypoxanthine derivative; and
When $R_1$ and $R_2$ are both amino groups, the compound of formula (I) is a 2,6-diaminopurine derivative.

Often, the compound of formula (I) is a guanine or adenine derivative.

Suitable examples of $R_3$ when an acyl group, include carboxylic acyl, such as $C_{1-7}$ alkanoyl and benzoyl optionally substituted in the phenyl ring as defined below for $R_5/R_6$. Preferred acyl groups include acetyl, propionyl, butyryl, heptanoyl and hexanoyl.

Suitable examples of $R_5$ and $R_6$ include hydrogen, methyl, ethyl, n- and iso-propyl, n-, sec-, iso- and tert-butyl, and phenyl optionally substituted by one, two or three groups or atoms selected from halogen, such as fluoro, chloro, bromo, and $C_{1-4}$ alkyl or $C_{1-4}$ alkoxy wherein the alkyl moiety is selected from those listed for $R_5/R_6$ above.

Examples of $R_7$ include methyl, ethyl, n- and iso-propyl, phenyl and benzyl optionally substituted by one or two of methyl, ethyl, n- and iso-propyl, methoxy, ethoxy, n- and iso-propoxy, fluoro, chloro or bromo.

Examples of pharmaceutically acceptable salts of the compound of formula (I) are acid addition salts formed with a pharmaceutically acceptable acid such as hydrochloric acid, orthophosphoric acid and sulphuric acid. Pharmaceutically acceptable salts also include those formed with organic bases, preferably with amines, such as ethanolamines or diamines; and alkali metals, such as sodium and potassium.

As the compound of formula (I) contains a phosphonate group, suitable salts include metal salts, such as alkali metal salts, for example sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tris-(2-hydroxyethyl)amine.

It will be appreciated that some of the compounds of formula (I), especially those wherein X is a moiety of structure (a), (b) or (c), have an asymmetric centre, and therefore are capable of existing in more than one stereoisomeric form. The invention extends to each of these forms individually and to mixtures thereof, including racemates. The isomers may be separated conventionally by chromatographic methods or using a resolving agent. Alternatively, the individual isomers may be prepared by asymmetric synthesis using chiral intermediates.

The compounds of formula (I) including their alkali metal salts may form solvates such as hydrates and these are included wherever a compound of formula (I) or a salt thereof is herein referred to.

It will be appreciated that, when $R_1$ is hydroxy in formula (I) the compound exists in the predominant tautomeric form of structure (IA):

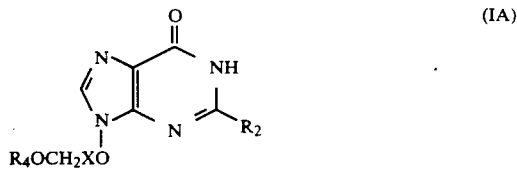

The invention also provides a process for the preparation of a compound of formula (I), or a pharmaceutically acceptable salt thereof, which process comprises either i) imidazole ring closure of a compound of formula (II):

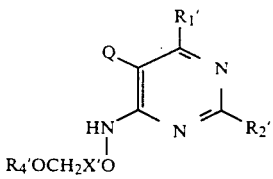

wherein Q is a group capable of cyclising to form an imidazole ring, such as amino or an amino derivative, for example, formylamino; or ii) pyrimidine ring closure of a compound of formula (III):

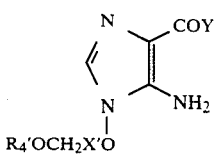

wherein Y is amino or $C_{1-6}$ alkoxy, with a condensing agent capable of cyclising to form a pyrimidine ring having a 2-$R_2'$ substituent, to give a compound of formula (I) wherein $R_1$ is hydroxy and $R_2$ is amino; or iii) condensing a compound of formula (IV):

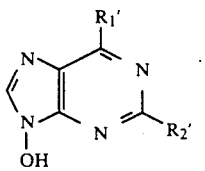

with a side chain intermediate of formula (V):

   (V)

wherein Z is a leaving group;
and wherein, in formulae (II) to (V), $R_1'$, $R_2'$, $X'$, $R_4'$ are $R_1$, $R_2$, $R_3$ and $R_4$ respectively, or groups or atoms convertible thereto; and thereafter, when desired or necessary, converting $R_1'$, $R_2'$, $X'$ and/or $R_4'$, when other than $R_1$, $R_2$, X and/or $R_4$ to $R_1$, $R_2$, X and/or $R_4$ respectively, and/or converting $R_1'$, $R_2'$, $X'$ and/or $R_4'$ when $R_1$, $R_2$, X and/or $R_4$, to other $R_1$, $R_2$, X and/or $R_4$.

Process i) may be carried out, preferably when Q is formylamino, using a cyclisation condensing agent, such as diethoxymethyl acetate or triethyl orthoformate, or by fusion.

Process ii) is preferably carried out in accordance with the methods described in EP-A-242482, the subject matter of which is incorporated herein by reference.

Process iii) may be carried out with suitable values for Z including hydroxy and halo, such as chloro, bromo and iodo, preferably iodo; or other groups readily displaceable by nucleophiles, such as mesyloxy or tosyloxy. The reaction preferably takes place in an inert solvent, such as dimethylformamide at 0°–50° C., preferably ambient temperature. When Z is hydroxy, the reaction takes place in the presence of a dehydrating agent, such as diethyl azodicarboxylate in the presence of triphenylphosphine. When Z is halo, the reaction preferably takes place in the presence of a base, such as potassium carbonate.

Examples of conversions of variable groups are as follows:

$R_1'$-$R_1$ a) An $R_1$ hydroxy group may be converted to $R_1'$ is chloro, by chlorination using a reagent such as phosphorus oxychloride, preferably in the presence of tetraethylammonium chloride and dimethylaniline (as acid acceptor) in $CH_3CN$ at reflux temperatures, according to the method described by M. J. Robins and B. Ozanski Can. J. Chem, 59, 2601 (1981).

b) An $R_1'$ chloro group may be converted to $R_1$ is hydroxy by hydrolysis using aqueous mineral acid, such as hydrochloric acid, or more preferably, using an organic acid, such as formic acid at elevated temperature, suitably 70°–150° C., preferably around 100° C.

c) An $R_1'$ chloro group may be converted to $R_1$ is amino by treatment with ammonia in a lower alkanol, such as ethanol or methanol in an autoclave at 100° C. for a period of about 7 hours, or alternatively, by treatment with sodium azide in dimethylformamide (forming an $R_1$ is $N_3$ intermediate), followed by reduction with ammonium formate/palladium or charcoal, in methanol.

d) An $R_1'$ alkoxy group, such as methoxy, may be converted to $R_1$ hydroxy by the methods of D. R. Haines, J. Med. Chem. 1987, 30, 943 and K. K. Ogilvie and H. R. Hanna, Can. J. Chem. 1984, 62, 2702.

e) An $R_1'$ protected amino group, such as tritylamino, may be converted to amino, by treatment with aqueous acetic acid, preferably 80% acetic acid at elevated temperature, around 80° C. $R_1'$ may also be phthalimido, which may be converted to amino by treatment with methyl hydrazine or hydrazine in an inert solvent, such as dichloromethane, at ambient temperature.

$R_2'$-$R_2$ a) $R_2'$ may be protected amino, such as formylamino, which may be converted to $R_2$ is amino by hydrolysis.

$X'$-$X$ a) $R_3$ hydrogen may be converted to $R_3$ acyl by conventional acylation procedures.

b) $R_3$ may be replaced by a protecting group, which may be removed by conventional deprotection methods.

Suitable examples of protecting groups and processes for their removal, are as described in EP-A-242482. Particularly suitable protecting groups include the benzyl group, removed by catalytic hydrogenation using palladium/charcoal, 80% acetic acid; the acetate group removed by acid hydrolysis, 2M HCl in ethanol; or the t-butyldimethylsilyl group removable by 80% acetic acid at elevated temperature, around 90° C.

$R_4'$-$R_4$ a) When $R_5$ and $R_6$ in $R_4$ are other than hydrogen, they may be converted to $R_5$ and $R_6$ are hydrogen, using a deesterifying reagent, such as trimethylsilyl bromide in an aprotic solvent such as dichloromethane or dimethylformamide at ambient temperature; as described by C. E. McKenna et. al. J.C.S. Chem. Comm., 1979, 739.

Selective conversion of one $R_5$ and $R_6$ to hydrogen, may be achieved by treatment with hydroxide ion, as described by Rabinowitz JACS 1960, 82, 4564.

b) $R_4'$ may be hydrogen, which may be converted to $R_4$, by treatment with $QR_4$ wherein Q is a leaving group and $R_4$ is as defined. Q is preferably a tosyloxy group.

Conditions for this reaction are i) preliminary formation of an alkoxide using a base, such as sodium hydride, in an aprotic solvent for example dimethylformamide ii) reaction with QR$_4$ at around ambient temperature. The reaction is as described A. Holy et. al. Collect. Czech. Chem. Comm. 1982, 47, 3447. In this case, R$_5$ and R$_6$ are other than hydrogen.

c) R$_4'$ may be hydrogen, which may be converted, when X is of moiety (a) wherein n is 1 and R$_3$ is hydrogen, to R$_4$ is CH$_2$PO(OH)(OR$_5$), by treatment with ClCH$_2$PCl$_2$ followed by treatment with a base, followed by OR$_5^-$, according to the method described by A. Holy et. al. Czech. Chem. Comm. 1985, 50, 1507; ibid 1987, 52, 2775.

It will be appreciated that the above conversions may take place in any desired or necesssary order, having regard to the final desired compound of formula (I).

Intermediates of formula (II) may be prepared from a corresponding compound of formula (VI):

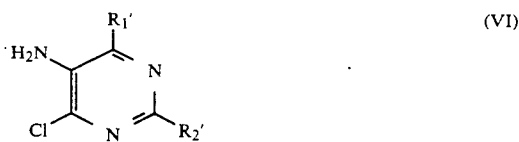

and via intermediates of formula (V) wherein Z is OH, as hereinbefore defined, according to the methods described in EP-A-242482 i.e. by converting the compound of formula (V) wherein Z is OH to the phthalimidooxy derivative followed by reaction with methylhydrazine, as described in Description 1 hereinafter.

The compound of formula (VI) wherein R$_1'$ is chloro and R$_2$ is amino, is a known compound as described by Temple et. al. J. Org. Chem., 40 (21), 3141, 1975.

The compound of formula (VI) wherein R$_1'$ is chloro and R$_2$ is hydrogen is a commercially available compound.

Intermediates of formula (III) may be prepared according to the methods described in EP-A-242482.

Compounds of the formula (IV) are prepared from compounds of formula (VI) wherein the 5-amino group is formylated, by reaction with R$_8$ONH$_2$ wherein R$_8$ is a protecting group, to give a compound of formula (VII):

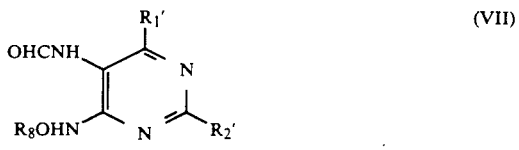

which may be cyclised with diethoxymethyl acetate, to give a compound of formula (IV) wherein the OH group is protected. Suitable values for R$_8$ include benzyl, removable by hydrogenation, and the tetrahydropyran-2-yl group removable by treatment with 80% acetic acid, at ambient temperature. The preparation of intermediates of formula (IV) is described in EP-A-313289 and 319228 (Beecham Group p.l.c.).

Intermediates of the formula (V) wherein Z is hydroxy are known compounds or are prepared by analogous methods to those used for structurally similar known compounds, such as according to the methods of description 1 a) and b) hereinafter.

It will be appreciated that, when X is of structure (a), (b) or (c) in the resulting compound of formula (I), synthesis of the intermediate of formula (V) wherein Z is hydroxy may involve selective deprotection of an intermediate wherein Z is protected hydroxy and R$_3$ is replaced by a protecting group.

Intermediates of formulae (II), (III) and (V) but wherein Z is replaced by an aminooxy group, and wherein R$_4'$ is R$_4$ as defined in formula (I), are believed to be novel and form an aspect of the invention.

Pharmaceutically acceptable salts may be prepared in conventional manner, for example, in the case of acid addition salts, by reaction with the appropriate organic or inorganic acid.

It will be appreciated that the invention provides a process for the preparation of a compound of formula (I) wherein X is of structure (a), (b) or (c) and R$_3$ is hydrogen, which process comprises the deprotection of a corresponding compound of formula (I) wherein R$_3$ is replaced by a protecting group. Preferred methods for deprotection, as hereinbefore described include removal of the benzyl, acetate or $^t$butyldimethylsilyl group.

The invention also provides a process for the preparation of a compound of formula (I) wherein R$_5$ and R$_6$ are both hydrogen, which process comprises the deesterification of a corresponding compound of formula (I) wherein R$_5$ and R$_6$ are the same alkyl or optionally substituted phenyl group.

The compounds of the invention are of potential use in the treatment of infections caused by viruses, especially lentiviruses such as visna virus and human immunodeficiency virus (strains 1 and 2); and also varicella-zoster virus and cytomegalovirus.

Some of the compounds may also be inhibitors of tumorogenic viruses and/or of potential use in the treatment of neoplastic diseases, i.e. cancer.

Compounds of the invention may be formulated for use in a pharmaceutical composition. Accordingly, in a further aspect of the invention, there is provided a pharmaceutical composition which comprises a compound of formula (I) or pharmaceutically acceptable salt thereof together with a pharmaceutically acceptable carrier or excipient.

A composition which may be administered by the oral route to humans may be compounded in the form of a syrup, tablet or capsule. When the composition is in the form of a tablet, any pharmaceutical carrier suitable for formulating such solid compositions may be used, for example magnesium stearate, starch, lactose, glucose, rice, flour and chalk. The composition may also be in the form of an ingestible capsule, for example of gelatin, to contain the compound, or in the form of a syrup, a solution or a suspension. Suitable liquid pharmaceutical carriers include ethyl alcohol, glycerine, saline and water to which flavouring or colouring agents may be added to form syrups. The compounds may also be presented with a sterile liquid carrier for injection.

The composition may also be formulated for topical application to the skin or eyes.

For topical application to the skin, the composition may be in the form of a cream, lotion or ointment. These formulations may be conventional formulations well known in the art, for example, as described in standard books of pharmaceutics and cosmetics, such as Harry's Cosmeticology published by Leonard Hill Books and the British Pharmacopaeia.

The composition for application to the eyes may be a conventional eye-drop composition well known in the art, or an ointment composition.

Preferably, the composition of this invention is in unit dosage form or in some other form that may be administered in a single dose. A suitable dosage unit might contain from 50 mg to 1 g of active ingredient, for example 100 to 500 mg.

Such doses may be administered 1 to 4 times a day or more usually 2 or 3 times a day. The effective dose of compound will in general be in the range of from 1.0 to 20 mg/kg of body weight per day or more usually 2.0 to 10 mg/kg per day.

No unacceptable toxicological effects are indicated at the above described dosage levels.

The invention also provides a method of treating viral infections in a human or non-human animal, which comprises administering to the animal an effective, non-toxic amount of a compound of formula (I) or a pharmaceutically acceptable salt thereof.

The invention also provides a compound of formula (I) or a pharmaceutically acceptable salt thereof for use as an active therapeutic substance, in particular for the treatment of viral infections.

The following examples illustrate the invention; the following descriptions illustrate the preparation of intermediates.

DESCRIPTION 1

Intermediates (V) for Examples 1–6 a) Diethyl 3-benzyloxypropoxymethylphosphonate

Paraformaldehyde (1.77 g, 59 mmol) was added to a solution of 3-benzyloxypropanol (9.8 g, 59 mmol) in dichloromethane (80 ml) and cooled to 0° C. Hydrogen chloride was then passed through the suspension until solution was complete and then for a further 30 minutes. The reaction mixture was then dried ($MgSO_4$), filtered and reduced in vacuo to give 3-benzyloxypropyl-chloromethyl ether as a colourless oil; $\nu_{max}$(film) 2860, 1130 cm$^{-1}$; $\delta_H$(CDCl$_3$) 1.90(2H, m, $CH_2\underline{CH_2}CH_2$), 3.52(2H, t, J6 Hz, $\underline{CH_2}OCH_2Ph$), 3.77(2H, t, J6 Hz, $CH_2O\underline{CH_2}Cl$), 4.50($\overline{2H}$, s, Ph$\underline{CH_2}O$), 5.53(2H, s, O$\underline{CH_2}$Cl), 7.40(5H, s, $C_6H_5$).

The crude α-chloro ether was stirred for 2 h at 140° C. with triethylphosphite (10.12 ml, 59 mmol) and for a further 60 h at 25° C. After evaporation under reduced pressure the residue was taken up in chloroform, washed twice with saturated sodium hydrogen carbonate and once with water. The chloroform extract was dried ($MgSO_4$), filtered and evaporated in vacuo. Column chromatography of the residue on silica, eluting with hexane/ethylacetate (1:3) gave diethyl 3-benzyloxypropoxymethyl phosphonate as a colourless oil (12.2 g, 65%); $\nu_{max}$(film) 2870, 1240 and 1050 cm$^{-1}$; $\delta_H$(CDCl$_3$) 1.37(6H, t, J7 Hz,(OCH$_2$CH$_3$)$_2$), 1.90(2H, m, CH$_2$CH$_2$CH$_2$), 3.50–3.95(6H, m, Ph$CH_2OCH_2$ and $CH_2O\underline{CH_2}P$), 4.20(4H, m,(CH$_3$CH$_2$O), 4.52($\overline{2H}$, s, PhCH$_2$O). 7.40(5H, s, $C_6H_5$).

b) Diethyl 3-hydroxypropoxymethylphosphonate

10% Palladium on charcoal (4.5 g) was added to a solution of diethyl 3-benzyloxypropoxymethylphosphonate (14.6 g, 46 mmol) in ethanol (250 ml) and 5M hydrochloric acid (4 ml) and the reaction stirred under an atmosphere of hydrogen for 6 h. The catalyst was removed by filtration through a glass-fibre paper and the ethanol evaporated under reduced pressure. The residue was then dissolved in chloroform, dried ($MgSO_4$), filtered and reduced in vacuo to give diethyl 3-hydroxypropoxymethylphosphonate as a colourless oil (8.97 g, 86%); $\nu_{max}$(film) 3419, 2935, 1241, 1029 cm$^{-1}$; $\delta_H$(CDCl$_3$) 1.46(6H, t, J7.1 Hz, (CH$_3$CH$_2$O)$_2$), 1.83(2H, m, CH$_2\underline{CH_2}$CH$_2$), 3.73–3.79(5H, m, $\underline{CH_2}$CH$_2\underline{CH_2}$ and OH ($\overline{D_2O}$ exchangeable)), 3.81(2H, d, J7.9 Hz, C$\underline{H_2}$P), 4.18(4H, m, (CH$_3\underline{CH_2}$O)$_2$).

c) Diethyl 3-(N-phthalimidooxy)propoxymethylphosphonate

A mixture of diethyl 3-hydroxypropoxymethyl phosphonate (8.90 g, 39.3 mmol) N-hydroxyphthalimide (7.70 g, 47.2 mmol) and triphenylphosphine (12.38 g, 47.2 mmol) in tetrahydrofuran (200 ml) was cooled to 0° C. and stirred during the addition of diethyl azodicarboxylate (7.43 ml, 47.2 mmol). The solution was then stirred for 24 h at 25° C. and evaporated to dryness. The residue was triturated twice with ether, evaporated to dryness then chromatographed in hexane/acetone (3:1) to give diethyl 3-(N-phthalimidooxy)propoxymethylphosphonate (8.8 g, 60%) as a colourless oil; $\nu_{max}$(film) 2990, 1785, 1740, 1250, 1030 cm$^{-1}$; $\delta_H$(CDCl$_3$) 1.51(6H, t, J7.0 Hz, (CH$_3$CH$_2$O)$_2$), 2.07(2H, m, CH$_2\underline{CH_2}$CH$_2$), 3.85(4H, m, $\overline{CH_2}$OC$\overline{H_2}$P), 4.19(4H, m,(CH$_3\underline{CH_2}$O)$_2$), 4.32(2H, t, J6.2 Hz, CH$_2$ON), 7.63–7.86(4H, m, $\overline{C_6H_4}$).

d) Diethyl 3-aminooxypropoxymethylphosphonate

A solution of diethyl 3-(N-phthalimidooxy)propoxymethyl phosphonate (8.80 g, 23.7 mmol) in dichloromethane (70 ml) was cooled to 0° C. and stirred during the addition of methyl hydrazine (2.11 ml, 33.5 mmol). The solution was then stirred at 25° C. for a further 2 h then filtered. After removal of the solvent in vacuo, the residue was triturated with ether. Concentration of the filtrate followed by chromatography in chloroform/methanol (30:1) afforded diethyl 3-aminooxypropoxymethyl phosphonate (5.07 g, 89%) as a pale yellow oil. $\nu_{max}$(film) 3313, 2984, 1242, 1053 cm$^{-1}$; $\delta_H$(CDCl$_3$) 1.37(6H, t, J7.0 Hz,(CH$_3$CH$_2$O)$_2$) 1.90(2H, m, CH$_2\underline{CH_2}$CH$_2$), 3.65(2H, t, J6.3 Hz, $\underline{CH_2}$OCH$_2$P), 3.74($\overline{2H}$, t, J6.29 Hz, CH$_2$ONH$_2$), 3.89($\overline{2H}$, d, J8.5 Hz,CH$_2$P), 4.18(4H, m,(C$\overline{H_3}$CH$_2$O)$_2$), 4.80–5.40(2H, br s, ON$\underline{H_2}$).

DESCRIPTION 2

Intermediates for Examples 1–4 a) 4-Chloro-6-[3-(diethoxyphosphorylmethoxy)propoxyamino]-2,5-diformamidopyrimidine A mixture of diethyl 3-aminooxypropoxymethylphosphonate (4 g,16.6 mmol), 4,6-dichloro-2,5-diformamidopyrimidine (3.9 g, 16.6 mmol) and diisopropylethylamine (8.67 ml, 49.8 mmol) in diglyme (80 ml) was heated at 100° C. for 2 h. After removal of the solvent under reduced pressure, the residue was chromatographed in chloroform/methanol (100:1, 50:1, 10:1) affording 4-chloro-6-[3-(diethoxyphosphorylmethoxy)-propoxyamino]-2,5-diformamidopyrimidine as a yellow oil (4.61 g, 63%); $\nu_{max}$(film) 3200, 2990, 1690, 1590, 1220, 1040 cm$^{-1}$; $\delta_H$[(CD$_3$)$_2$SO] 1.22(6H, t, J7 Hz, (CH$_3$CH$_2$O)$_2$), 1.85(2H, m, CH$_2\underline{CH_2}$CH$_2$), 3.65(2H, t, J6.3 Hz, $\underline{CH_2}$OCH$_2$P), 3.40(2H, d, J8.2 Hz, CH$_2$P), 3.92(2H, t, J6 Hz, CH$_2$ON), 4.04(4H, m, (CH$_3$CH$_2$O)$_2$), 8.15(1H, s, CHO), 9.25(1H, br.s, CHO), 9.43(1$\overline{H}$, br.s, D$_2$O exchangeable, NH), 10.76(1H, br s, D$_2$O exchangeable, NH), 10.86(1H, br.s,D$_2$O exchangeable, NH); Found: M+ 439.1015; $C_{14}H_{23}ClN_5O_7P$ requires: M+ 439.1024.

b) 6-Chloro-9-[3-(diethoxyphoschorylmethoxy)procoxy]-2-formamidopurine

A solution of 4-chloro-6-[3-(diethoxyphosphorylmethoxy)propoxyamino]-2,5-diformamidopyrimidine (4.48 g, 10 mmol) in diethoxymethyl acetate (40 ml) was heated at 120° C. for 2.5 h. After removal of the solvent in vacuo. the residue was dissolved in methanol (50 ml) and 0.88 ammonia (2 ml) then stirred at 25° C. for 2 h. The reaction was then reduced in vacuo and co-evaporated twice with methanol before chromatography of the residue in chloroform/methanol (100:1) to give 6-chloro-9-[3-(diethoxyphosphorylmethoxy)-propoxy]-2-formamidopurine (2.92 g, 69.2%) as a yellow oil. $\nu_{max}$(film) 3117,1709, 1612, 1577, 1508, 1244, 1027 cm$^{-1}$; $\delta_H$[(CD$_3$)$_2$SO] 1.23(6H, t, J7 Hz,(CH$_3$CH$_2$O)$_2$), 1.97(2H, m, CH$_2$CH$_2$CH$_2$), 3.74(2H, t, J6.1Hz, CH$_2$OCH$_2$P), 3 84(2H, d, J8.0 Hz, CH$_2$P), 4.04(4H, m, (CH$_3$CH$_2$O)$_2$), 4.48(2H, t, J6.3 Hz, CH$_2$ON), 8.83(1H, s, H-8), 9.37(1H, br.s, CHO), 11.30(1H, br.s, D$_2$O exchangeable, NH); Found: C, 40.05; H, 5.22; N, 16.85%; M+, 421.0921. $C_{14}H_{23}ClN_5O_7P$ requires: C, 39.87; H, 5.02; N, 16.60%; M+, 421.0918.

DESCRIPTION 3

Intermediates for Examples 5 and 6.

a) 4-Chloro-6-[3-(diethoxyphosphorylmethoxy)proooxyamino]-5-formamidopyrimidine A mixture of diethyl 3-aminooxypropoxymethylphosphonate (1.0 g, 4.15 mmol), 4,6-dichloro-5-formamidopyrimidine (0.80 g, 4.15 mmol) and diisopropylethylamine (2.16 ml, 12.45 mmol) in diglyme (25 ml) was heated at 100° C. for 2 h. The solvent was then removed in vacuo and the residue chromatographed in chloroform/methanol (50:1) to give 4-chloro-6-[3-(diethoxyphosphorylmethoxy)propoxyamino]-5-formamidopyrimidine (1.1g, 67%) as a brown oil; $\nu_{max}$(film) 1600, 1570, 1220, 1030 cm$^{-1}$; $\delta_H$[(CD$_3$)$_2$SO] 1.23(6H, t, J7.2 Hz, (CH$_3$CH$_2$O)$_2$), 1.85(2H, m, CH$_2$CH$_2$CH$_2$), 3.63(2H, t, J6 Hz, CH$_2$OCH$_2$P), 3.79(2H, d, J8.3 Hz, CH$_2$P), 3.94(2H, t, J6.1Hz, CH$_2$ON), 4.04(4H, m, (CH$_3$CH$_2$O)$_2$), 8.15(1H, s, H-2), 9.50(1H, br s, D$_2$O exchangeable, NH), 10.50-12.00(1H, br s, NH); Found: C, 39.37; H, 5.69; N, 13.82%; M+ 396.0963; $C_{13}H_{22}ClN_4O_6P$ requires: C, 39.35; H, 5.59; N, 14.12%; M+ 396.0966.

b) 6-Chloro-9-3-(diethoxyphosphorylmethoxy)propoxy]-purine

4-Chloro-6-[3-(diethoxyphosphorylmethoxy)propoxyamino -5-formamidopyrimidine 1.06 g, 2.67 mmol) was heated at 120° C. for 3 h in diethoxymethyl acetate (15 ml). On removal of the solvent in vacuo the residue was taken up in methanol (15 ml) and 0.88 ammonia (1ml) then stirred at 25° C. for 1.5 h, dried in vacuo and co-evaporated twice with methanol. Chromatography in chloroform/methanol (50:1) afforded 6-chloro -9-[3-(diethoxyphosphorylmethoxy)propoxy]purine (0.79 g, 78%) as a yellow oil; $\nu_{max}$(film) 1564, 1333, 1253, 1028 cm$^{-1}$; $\delta_H$(CDCl$_3$) 1.35(6H, t, 7 Hz, (CH$_3$CH$_2$O)$_2$), 2.13(2H, m, CH$_2$CH$_2$CH$_2$), 3.87(4H, m, CH$_2$OCH$_2$P), 4.18(4H, m, (CH$_3$CH$_2$O), 4.61(2H, t, J6 Hz, NOCH2), 8.43 and 8.78(2H, 2s, H-8 and H-2); Found:C, 40.41; H 5.43; N, 13.88%; $C_{13}H_{20}ClN_4O_5P$.0.5H$_2$O requires: C 40.27; H, 5.46; N, 14.25%.

DESCRIPTION 4

Intermediates (V) for Examples 8-14 a) 5-Phthalimidooxymethyl-1,3-dioxane

A mixture of 5-hydroxymethyl-1,3-dioxane (3.90 g 33 mmol), N-hydroxyphthalimide (6.46 g, 39.6 mmol and triphenylphosphine (10.39 g, 39.6 mmol) in tetrahydrofuran (150 ml) was cooled to 0° C. and stirred during the addition of diethyl azodicarboxylate (6.24 ml 39.6 mmol). The solution was then stirred for 16 h at 25° C. and evaporated to dryness. The residue was triturated twice with ether, evaporated to dryness then chromatographed in chloroform/methanol (40:1) to give 5-phthalimidooxymethyl-1,3-dioxane (6.63 g 76.3%) as a white solid; m.p. 98–106° C.: $\nu_{max}$(KBr) 1780, 1735, 1470, 1400, 1160 cm$^{-1}$; $\delta_H$(CDCl$_3$) 2.20(1H. m, CH), 4.07(4H, m, OCH$_2$CHCH$_2$O), 4.37(2H, d, J6.88 Hz, CH$_2$ON), 4.86(2H, m, OCH$_2$O), 7.81(4H, m, C$_6$H$_4$): Found: C,59.31; H, 5.03; N, 5.31%; $C_{13}H_{13}NO_5$ requires: C, 59.31; H, 4.98; N, 5.32%; m/z 264(MH+. 100%).

b) Diethyl 2-acetoxymethyl-3-(N-phthalimidooxv)propoxymethylphosphonate

5-Phthalimidooxymethyl-1,3-dioxane (6.32 g, 24 mmol) was added portionwise to freshly distilled acetyl bromide (11 ml) at 0° C. and the reaction mixture was stirred at 25° C. for 25 minutes. Evaporation in vacuo gave N-(3-acetoxy-2-bromomethoxymethyl)propoxyphthalimide as a pale yellow oil. $\delta_H$(CDCl$_3$) 2.13(3H, s, CH$_3$CO), 2.53(1H, m, CH), 3.94(2H, d, J6 Hz, CH$_2$), 4.30(4H, d, J6 Hz, 2×CH$_2$), 5.76(2H, s, CH$_2$Br), 7.90(4H, s, C$_6$H$_4$).

The crude c-bromo ether was stirred for 2 h at 140° C. with triethylphosphite (4.2 ml, 24 mmol) and for a further 16 h at 25° C. The reaction mixture was evaporated to dryness and the residue chromatographed in hexane/acetone (1:1, 1:3) to give diethyl 2-acetoxymethyl-3-(N-phthalimidooxy)propoxymethylphosphonate (6.8 g, 64%) as a pale yellow oil. $\nu_{max}$(film) 1790, 1730, 1370, 1240, 1020 cm$^{-1}$; $\delta_H$(CDCl$_3$) 1.34(6H, t, J7 Hz, (CH$_3$CH$_2$O)$_2$), 2.08(3H, s, CH$_3$CO), 2.50(1H, m, CH), 3.81(2H, d, J5.8 Hz, CH$_2$), 3.85(2H, d, J8.25 Hz, CH$_2$P), 4.17(4H, m, (CH$_3$CH$_2$O)$_2$), 4.29(4H, m, 2×CH$_2$), 7.80(4H, m, C$_6$H$_4$); m/z 444 (MH+, 6%).

c) Diethyl 2-acetoxymethyl-3-aminooxypropoxymethylphosphonate

A solution of diethyl 2-acetoxymethyl-3-(N-phthalimidooxy)propoxymethylphosphonate (6.64 g, 15 mmol) in dichloromethane (40 ml) was cooled to 0° C. and stirred during the addition of methyl hydrazine (0.84 ml, 15.8 mmol). The solution was stirred at 25° C. for a further 2.5 h then filtered. After removal of the solvent in vacuo, the residue was chromatographed in chloroform/methanol (50:1) to give diethyl 2-acetoxymethyl-3-aminooxypropoxymethylphosphonate as a pale yellow oil (3.9 g, 83%). $\nu_{max}$ (film) 3310, 1736, 1370, 1240, 1020 cm$^{-1}$; $\delta_H$(CDCl$_3$) 1.35(6H, t, J7 Hz, (CH$_3$CH$_2$O)$_2$), 2.06(3H, s, CH$_3$CO), 2.36(1H, m, CH), 3.62(2H, m, CH$_2$), 3.71(2H, d, J6.3 Hz, CH$_2$), 3.78(2H, d, J8.25 Hz, CH$_2$P), 4.14(6H, m, (CH$_3$CH$_2$O)$_2$ and CH$_2$), 5.44(2H, br s, D$_2$O exchangeable, NH$_2$); Found: MH$^+$ 314.1350; C$_{11}$H$_{14}$NO$_7$P requires: MH$^+$ 314.1369.

DESCRIPTION 5

Intermediates (II) for Examples 8 and 10 a)

4-[(2-Acetoxymethyl-3-diethoxyphosphorylmethoxy)-propoxyamino]-6-chloro-2,5-diformamidopyrimidine A mixture of diethyl 2-acetoxymethyl-3-aminooxypropoxymethylphosphonate (2.5 g, 7.98 mmol), 4,6-dichloro-2,5-diformamidopyrimidine (1.88 g, 7.98 mmol) and diisopropylethylamine (4.17 ml, 23.9 mmol) in diglyme (40 ml) was heated at 100° C. for 2 hr. After removal of the solvent under reduced pressure, the residue was chromatographed in chloroform/methanol (30:1) affording 4-[(2-acetoxymethyl-3-diethoxyphosphorylmethoxy)propoxyamino]-6-chloro-2,5-diformamidopyrimidine as a yellow oil (2.82 g, 69%). $\nu_{max}$ (film) 1710, 1590, 1240, 1020 cm$^{-1}$; $\delta$H[(CD$_3$)$_2$SO] 1 22(6H, t, J7 Hz, (CH$_3$CH$_2$O)$_2$), 2.02 (3H, s, CH$_3$CO), 2.31(1H, m, CH). 3 63(2H, m, CH$_2$), 3.81(2H, d, J7.97 Hz, CH$_2$P), 3.91(2H, m, CH$_2$); 4.03(4H, m, (CH$_3$CH$_2$O)$_2$), 8.15(1H, s, CHO); 9.26(1H, d, J8.8 Hz, CHO), 9.43(1H, br s, D$_2$O exchangeable, NH), 10.83(2H, br m, D$_2$O exchangeable, 2×NH); Found: C, 38.35; H, 5.34; N, 13.38%; C$_{17}$H$_{27}$ClN$_5$O$_9$P.H$_2$O requires: C, 38.54; H, 5.52; N, 13.22%; m/z(FAB+ve ion, thioglycerol) MH$^+$ 512.

b)

9-[(2-Acetoxymethyl-3-diethoxyphosphorylmethoxy)-propoxy]-6-chloro-2-formamidopurine A solution of 4-[(2-acetoxymethyl-3-diethoxyphosphorylmethoxy)propoxyamino]-6-chloro-2,5-diformamidopyrimidine (2.78 g, 5.43 mmol) in diethoxymethyl acetate (20 ml) was heated at 120° C. for 2 h. After removal of the solvent in vacuo. the residue was dissolved in methanol (20 ml) and 0.88 ammonia (1ml) then stirred at 25° C. for 2.5 h. The reaction mixture was then reduced in vacuo and coevaporated twice with methanol before chromato-graphy of the residue in chloroform/methanol (70:1) to give 9-[(2-acetoxymethyl-3-diethoxy phosphorylmethoxy)propoxy]-6-chloro-2-formamidopurine (2.04 g, 76%) as a pale yellow oil. $\nu_{max}$ (film) 1710, 1613, 1508, 1389, 1240, 1027 cm$^{-1}$; $\delta_H$(CDCl$_3$) 1.34(6H, t, J7 Hz, (CH$_3$CH$_2$O)$_2$), 2.10(3H, s, CH$_3$CO), 2.52(1H, m, CH), 3.87(2H, m, CH$_2$OCH$_2$P), 3.92(2H, d, J8.53, CH$_2$P), 4.21(4H, m, (CH$_3$CH$_2$O)$_2$), 4.28(2H, d, J6.3 Hz, CH$_2$OCO), 4.54(2H, m, CH$_2$ON), 8.20(1H, s, H-8), 9.52(2H, m, NHCHO); Found: C, 40.74; H, 5.24; N, 13.90%; C$_{17}$H$_{25}$ClN$_5$O$_8$P.0.5H$_2$O requires: C, 40.60; H, 5.21; N, 13.93%; m/z 494 (MH$^+$, 5%).

DESCRIPTION 6

Intermediates (II) for Example 12 a)

4-(2-Acetoxymethyl-3-diethylphosphorylmethoxy)-propoxyamino]-6-chloro-5-formamidopyrimidine A mixture of diethyl 2-acetoxymethyl-3-aminooxypropoxymethylphosphonate (0.5 g, 1.6 mmol), 4,6-dichloro-5-formamidopyrimidine (0.31 g, 1.6 mmol), and diisopropylethylamine (0.84 ml, 4.8 mmol) in diglyme (15 ml) was heated at 100° C. for 2 h. The solvent was then removed in vacuo and the residue chromatographed in chloroform/ methanol (50:1) to give 4-[(2-acetoxymethyl-3-diethylphosphorylmethoxy)propoxyamino]-6-chloro-5-formamidopyrimidine (0.31 g. 41%) as a brown oil; $\nu_{max}$ (film) 1740, 1700, 1630, 1570. 1370, 1240, 1030 cm$^{-1}$; $\delta_H$[(CD$_3$)$_2$SO] 1.22(6H, t, J7 Hz, (CH$_3$CH$_2$O)$_2$), 2.01(3H, s, CH$_3$CO), 2.32(1H, m. CH), 3.61(2H, m, CH$_2$OCH$_2$P), 3.80(2H, d, J7.97 Hz. CH$_2$P), 3.93(2H, m, CH$_2$ON), 4.03(6H, m. (CH$_3$CH$_2$O)$_2$ and CH$_2$OCO), 8.15(1H, br s, H-2); Found: C, 40.45; H, 5.71; N, 11.24%: C$_{16}$H$_{26}$N$_4$O$_8$PCl.0.6 H$_2$O requires: C, 40.07; H, 5.53; N. 11.68%; m/z (FAB+ve ion) MH$^+$469.

b)

9-[(2-Acetoxymethyl-3-diethoxyphosphorylmethoxy)-propoxy]-6-chloropurine

4-[(2-Acetoxymethyl-3-diethylphosphorylmethoxy)-propoxyamino]-6-chloro-5-formamidopyrimidine (0.70 g, 11.5 mmol) was heated at 120° C. for 2 h in diethoxymethyl acetate (7 ml). On removal of the solvent in vacuo the residue was taken up in methanol (7 ml) and 0.88 ammonia (0.5 ml) then stirred at 25° C. for 2 h, dried in vacuo and coevaporated twice with methanol. Chromatography in chloroform/methanol (50:1). afforded 9-[(2-acetoxymethyl -3-diethyoxyphosphorylmethoxy)propoxy]-6-chloropurine (0.44 g, 65%) as a colourless oil; $\nu_{max}$ (film) 1740, 1560, 1330, 1240, 1020 cm$^{-1}$; $\delta_H$(CDCl$_3$) 1.34(6H, t, J7.15 Hz, CH$_3$CH$_2$O)$_2$), 2.10(3H, s, CH$_3$CO), 2.56 (1H, m, CH), 3.84(2H, d, J7.98 Hz, CH$_2$P), 3.85(2H, m, CH $_2$OCH$_2$P), 4.17(4H, m, (CH$_3$CH$_2$O)$_2$), 4.33(2H, d, J5.8 Hz, CH$_2$ON), 4.57(2H, m, CH$_2$OCO), 8.45 and 8.77(2×1H, 2×s, H-8 and H-2); Found: C,41.55; H, 5.37; N, 12.10%; M$^+$450.1061; C$_{16}$H$_{24}$N$_4$O$_7$PCl.0.5H$_2$O requires: C, 41.79; H, 5.59; N, 12.18%; M$^+$450.1071.

DESCRIPTION 7

Intermediates (V) for Examples 15-18 a) Diethyl allyloxymethylphosphonate

To a hexane washed suspension of 60% sodium hydride (262mg, 6.5 mmol) in diethyl ether (10 ml) was added diethyl hydroxymethylphosphonate (1g, 5.95 mmol) and the reaction mixture stirred for 1 hour at 20° C. under nitrogen. Allyl bromide (0.94 g, 0.67 ml, 7.7 mmol) was then added dropwise and the reaction mixture stirred for 2 hours at 20° C. The solids were filtered off and the filtrate diluted with dichloromethane (30 ml). The solution was washed with water (2×30 ml), dried (MgSO$_4$) and the solvent evaporated to give diethyl allyloxymethylphosphonate (0.85 g, 69%) as a clear liquid needing no further purification. $\nu_{max}$ (film) 1260, 1030 and 960 cm$^{-1}$; $\delta_H$(CDCl$_3$) 1.34(6H, t, J7.3 Hz, 2×CH$_3$), 3.71(2H, d, J8.3 Hz, CH$_2$P), 4.17(6H, m, 2×CH$_2$CH$_3$+CH$_2$OCH$_2$P), 5.28(2H, m, CH$_2$=CH), 5.88(1H, m, CH$_2$=CH).

b) Diethyl 2,3-dihydroxypropoxymethylphosphonate

To a solution of diethyl allyloxymethylphosphonate (4.2 g. 20.2 mmol) in an acetone (50 ml) and water (25 ml) mixture, was added osmium tetroxide (1 crystal) and 4-methylmorpholine-N-oxide (3.8 g, 32.3 mmol). The reaction mixture was stirred at 20° C. under nitrogen until no more starting alkene was present (6 days). The solvents were evaporated under high vacuum and the residue chromatographed on silica eluting with chloroform-methanol 10:1 affording diethyl 2,3-dihydroxypropoxymethylphosphonate (4.2 g, 86%) as a clear liquid. $\nu_{max}$(film) 3400, 1650, 1230, 1100, 1030 and 960 cm$^{-1}$; $\delta_H$ (CDCl$_3$) 1.35(6H, t, J7.3 Hz, 2×CH$_2$CH$_3$), 3.20(2H, s, D$_2$O exchangeable, 2×OH), 3.62(5H, m, CH$_2$OH+CHOH+CH$_2$OCH$_2$P), 3.79(2H, d, 8.2 Hz, CH$_2$P), 4.14(4H, m, 2×CH$_2$CH$_3$); m/z 243 (MH$^+$, 13%); Found: C,38.50; H,7.70%; C$_8$H$_{19}$O$_6$P.0.4-H$_2$O requires C,38.52; H,7.94%.

c) Diethyl 3-t-butyldimethylsilyloxy-2-hydroxypropoxymethylphosphonate

To a solution of diethyl 2,3-dihydroxypropoxymethylphosphonate (4.15 g, 17.1mmol), triethylamine (1.9 g, 2.62 ml, 18.81 mmol), 4-dimethylaminopyridine (84mg, 0.7 mmol) and t-butyldimethylchlorosilane (2.92 g, 19.4 mmol) in dichloromethane (50 ml) was stirred for 16 hours at 20° C. under nitrogen. The solution was washed with water (50 ml), saturated ammonium chloride (50 ml) and dried (Na$_2$SO$_4$). The solvents was evaporated to leave a yellow oil which was chromatographed on silica eluting with ethyl acetate affording diethyl 3-t-butyldimethylsilyloxy-2-hydroxypropoxymethylphosphonate (4.35 g, 71%) as a pale lemon liquid. $\nu_{max}$ (film) 3400, 1460, 1240, 1100, 1020 and 960 cm$^{-1}$; $\delta_H$ (CDCl$_3$) 0.05(6H, s, (CH$_3$)$_2$Si), 0.86(9H, s,(CH$_3$)$_3$C), 1.31(6H, t, J7.3 Hz, 2×CH$_2$CH$_3$), 2.50(1H, br.s, D$_2$O exchangeable, OH), 3.70(7H, m, CH$_2$OSi+CHOH+CH$_2$OCH$_2$P), 4.12(4H, m, 2×CH$_2$CH$_3$); m/z 357(MH$^+$,3%), 341 (M-CH$_3$+,4%); Found: C,46.89; H,9.23%; C$_{14}$H$_{33}$O$_6$PSi requires C,47 17; H,9.33% d) Diethyl 3-t-butyldimethylsilVloxv-2-(N-phthalimidoxy)propoxymethYlphosphonate A solution of diethyl 3-t-butyldimethylsilyloxy-2-hydroxypropoxymethylphosphonate (0.9 g, 2.53 mmol), N-hydroxyphthalimide (0.49 g, 3.03 mmol), and triphenylphosphine (0.8 g, 3.03 mmol) in dry tetrahydrofuran (50 ml) was cooled to O° C. and treated with diethyl azodicarboxylate (0.66 g, 0.6 ml, 3.8 mmol) and stirred at 20° C. for 16 hours. The solvent was evaporated, the semi-solid residue triturated with ether (2×50 ml) and filtered. The ether was evaporated and the oil chromatographed on silica eluting with ethyl acetatemethanol 50:1 affording diethyl 3-t-butyldimethylsilyloxy-2-(N-phthalimidoxy)propoxymethylphosphonate (1 g, 79%) as a pale yellow oil. $\nu_{max}$ (film) 1790, 1730, 1460, 1370, 1250, 1020 and 960 cm$^{-1}$; $\delta_H$(CDCl$_3$) 0.05(6H,s,(CH$_3$)$_2$Si), 0.85(9H, s, (CH$_3$)$_3$C), 1.32(6H, t, J7.3 Hz, 2×CH$_2$CH$_3$), 3.90(6H, m, CH$_2$OSi+CH$_2$OCH$_2$P), 4.11(4H, m, 2×CH$_2$CH$_3$), 4.42(1H, m, CHON), 7.80(4H, m, ArH). Found: C,52.55; H,7.31; N,2.69%; MH$^+$502.2040; C$_{22}$H$_{36}$NO$_8$PSi requires C,52.68; H,7.23; N,2.79%; MH$^+$ 502.2026.

e) Diethyl 2-aminooxy-3-t-butyldimethylsilyloxypropoxymethylphosphonate

A solution of diethyl 3-t-butyldimethylsilyloxy-2-(N-phthalimidoxy)propoxymethylphosphonate (3.7 g, 7.39 mmol) in dichloromethane (100 ml) was cooled to 0° C. during the addition of methylhydrazine (0.68 g, 0.79 ml, 14.8 mmol) and then stirred for 2 hours at 20° C. The reaction mixture was filtered, the solvent evaporated and the residue suspended in ether and filtered again. The ether was evaporated and the residual oil chromatographed on silica eluting with ethyl acetate affording diethyl 2-aminooxy-3-t-butyldimethylsilyloxypropoxymethylphosphonate (1.7 g, 63%) as a clear oil. $\nu_{max}$ (film) 3480, 3320, 1590, 1460, 1250, 1100, 1050 and 960 cm$^{-1}$; $\delta_H$(CDCl$_3$) 0.05(6H, s, (CH$_3$)$_2$Si), 0.86(9H, s (CH$_3$)$_3$C), 1.32(6H, t, J7.3 Hz, 2×CH$_2$CH$_3$), 3.70(7H m, CH$_2$OSi+CHONH$_2$+CH$_2$OCH$_2$P), 4.11(4H, m 2×CH$_2$CH$_3$), 4.80(2H, br.s, D$_2$O exchangeable, NH$_2$) Found: C,45.24; H,9.22; N,3.70%; MH$^+$372.1947 C$_{14}$H$_{34}$NO$_6$PSi requires C,45.26; H,9.23; N,3.77% MH$^+$ 372.1971.

DESCRIPTION 8

Intermediates for Examples 15, 16, 19 and 20 a) 4-(1-t-Butyldimethylsilyloxy-3-diethoxyphosphorylmethoxyorop-2-oxyamino)-6-chloro-2,5-diformamidopyrimidine A mixture of diethyl 2-aminooxy-3-t-butyldimethylsilyloxypropoxymethylphosphonate (0.8 g, 2.16 mmol). 4,6-dichloro-2,5-diformamidopyrimidine (0.51 g, 2.16 mmol) and diisopropylethylamine (0.84 g, 1.12 ml, 6.47 mmol) in diglyme (20 ml) was stirred for 3 hours at 105° C. The solvent was evaporated and the residual oil chromatographed on silica eluting with chloroformmethanol 40:1 affording 4-(1-t-butyldimethylsilyloxy -3-diethoxyphosphorylmethoxyprop-2-oxyamino)-6-chloro-2,5-diformamidopyrimidine (0.74 g, 60%) as a yellow foam. $\nu_{max}$ (KBr) 3220, 1700, 1590, 1470, 1250, 1020 and 960 cm$^{-1}$; $\delta_H$ (CDCl$_3$) 0.90(6H, s, (CH$_3$)$_2$Si), 0.89(9H, s, (CH$_3$)$_3$C), 1.35(6H, t, J7.2 Hz, 2×CH$_2$CH$_3$), 3.85(7H, m, CH$_2$OSi+CHON+CH$_2$OCH$_2$P), 4.17(4H, m, 2×CH$_2$CH$_3$), 8.06(1H, br.s, D$_2$O exchangeable, NH), 8.32(1H, s, CHO), 8.70(1H, br.s, D$_2$O exchangeable, NH), 9.38 (1H, J10.1Hz, CHO), 9.80(1H, br.s, D$_2$O exchangeable, NH). Found: C,42.16; H,6.34; N,12.29%; M$^+$569.1845; C$_{20}$H$_{37}$N$_5$O$_8$ClPSi requires C,42.14; H,6.54; N,12 29%; M$^+$ 569.1838.

b) 9-(1-t-Butyldimethylsilyloxy-3-diethoxyphosphorylmethoxyprop -2-oxy)-6-chloro-2-formamidopurine A solution of 4-(1-t-butyldimethylsilyloxy-3-diethoxyphosphorylmethoxyprop-2-oxyamino)-6-chloro -2,5-diformamidopyrimidine (0.68 g, 1.19 mmol) in diethoxymethylacetate (10 ml) was stirred at 120° C. for 4 hours. The solvent was evaporated under high vacuum, the residue dissolved in methanol (10 ml) and 0.88 ammonia (0.3 ml) and stirred for 1 hour at 20° C. After evaporation to dryness, the residue was chromatographed on silica eluting with chloroform-methanol 40:1 affording 9-(1-t-butyldimethylsilyloxy-3-diethoxyphosphorylmethoxyprop-2-oxy)-6-chloro-2-formamidopurine (0.32 g, 49%) as a pale yellow oil. $\nu_{max}$ (film) 3420, 1710, 1620, 1580, 1510, 1440, 1390, 1250 and 1030 cm$^{-1}$; $\delta_H$(CDCl$_3$) 0.80(6H, s, (CH$_3$)$_2$Si), 0.87(9H, s, (CH$_3$)$_3$C), 1.30(6H, t, J7.2 Hz, 2×CH$_2$CH$_3$), 3.86(6H, m, CH$_2$OSi+CH$_2$OCH$_2$P), 4.15(4H, m, 2×CH$_2$CH$_3$), 4.50(1H, m, CHON); 8.26(1H, s, H-8); 9.00(1H, br.d, J10.5 Hz, D$_2$O exchangeable, NHCHO), 9.53(1H, d, J10.5 Hz, NHCHO). Found: C,43.02; H,6.49; N,12.18%; MH$^+$552.1812. C$_{20}$H$_{35}$N$_5$O$_7$ClPSi.0.5H$_2$O requires C,42.82; H,6.47; N,12.47%; MH$^+$ 552.1810.

c) 6-Chloro-9-1-(diethoxyphosphorylmethoxy)-3-hydroxyprop-2-oxy]-2-formamidopurine A solution of 9-[1-(t-butyldimethylsilyloxy) -3-(diethoxyphosphorylmethoxy)prop-2-oxy]-6-chloro-2-formamidopurine (100mg, 0.18 mmol) in tetrahydrofuran (5 ml) was treated, with tetrabutylammonium fluoride (60mg, 0.18 mmol) and the solution stirred for 4 h at 20° C. The solvent was reduced in vacuo and the residue partitioned between saturated sodium hydrogen carbonate and dichloromethane. The dichloromethane was separated and dried ($MgSO_4$) and the solvent evaporated in vacuo. The residue was chromatographed on silica, eluting with chloroform-methanol 20:1, affording 6-chloro-9-[1-(diethoxyphosphorylmethoxy)-3-hydroxyprop-2-oxy]2-formamidopurine (30mg, 37%) as a clear oil. $\nu_{max}$ (film) 3400, 3250, 1700, 1610, 1570 and 1500 $cm^{-1}$; $\delta_H$ ($CDCl_3$) 1.37 (6H, t, J7.1 Hz, $2 \times CH_2CH_3$), 3.84–3.96 (7H, m, $CH_2OH + CH_2OCH_2P$), 4.21 (4$\overline{H}$, m, $2 \times C\underline{H}_2CH_3$), 4.57 (1H, m, CHON), 8.37 (1H, s, H-8), 8.67 (1H, d, J10.1 Hz, $D_2O$ exchangeable, NH), 9.50 (1H, d, J10.1 Hz, CHO); m/z (FAB+ve Ion) 438 (MH+).

DESCRIPTION 9

Intermediates for Example 17 a)

4-(1-t-Butyldimethylsilyloxy-3-diethoxyohosphorylmethoxyprop-2-oxyamino)-6-chloro-5-formamidocyrimidine A mixture of diethyl 2-aminooxy-3-t-butyldimethylsilyloxypropoxymethylphosphonate (0.75 g, 2.02 mmol), 4,6-dichloro-5-formamidopyrimidine (0.39 g, 2.02 mmol) and diisopropylethylamine (0.78 g, 6.06 mmol) in diglyme (20 ml) was stirred at 105° C. for 4 hours. The solvent was evaporated and the residue chromatographed on silica eluting with ethyl acetate affording 4-(1-t-butyldimethylsilyloxy-3-diethoxyphosphorylmethoxyprop-2-oxyamino)-6-chloro-5-formamidopurine (0.44 g, 42%) as a yellowish solid, m.p. 111–115° C. $\nu_{max}$ (KBr) 3420, 1660, 1640, 1590, 1530, 1240, 1090, 040 and 840 $cm^{-1}$; $\delta_H$ [($CD_3$)$_2$SO] 0.08(6H, s, ($CH_3$)$_2$Si), 0.89(9H, s, ($CH_3$)$_3$C), 1.27(6H, t, J7.2 Hz, $2 \times CH_2CH_3$), 3.89(7H, m, $CH_2OSi + CHON + C\underline{H}_2OCH_2\overline{P}$), 4.08(4H, m, $2 \times C\underline{H}_2CH_3$), 8.30(1H, br.s, $\overline{H}$-2/CHO); 8.90(1H, br.s, H-2/$\overline{CHO}$), 7.5–11 6(2H, m, $D_2O$ exchangeable, $2 \times NH$); m/z 526 M,+26%); Found: C,43.76; H,6.52; N,10.56%; $C_{19}H_{36}N_4O_7ClPSi$ requires C, 43.30; H,6.88; N, 10.63%.

b)

9-(1-t-Butyldimethylsilyloxy-3-diethoxyphoschorylmethoxyprop-2-oxy)-6-chloropurine A solution of 4-(1-t-butyldimethylsilyloxy-3-diethoxyphosphorylmethoxyprop-2-oxyamino)-6-chloro-5-formamidopyrimidine (0.4 g, 0.76 mmol) in diethoxymethyl acetate (10 ml) was stirred at 120° C. for 4 hours. The solvents were evaporated, the residue dissloved in methanol (10 ml) and 0.88 ammonia (0.3 ml) and stirred for 1 hour. After evaporation, the residue was chromatographed on silica eluting with ethyl acetate and then with chloroform to give 9-(1-t-butyldimethylsilyloxy -3-diethoxyphosphorylmethoxyprop-2-oxy)-6-chloropurine (0.31 g, 80%) as a yellow oil. $\nu_{max}$ (film) 3480, 1600, 1540, 1340, 1260, 1030, and 840 $cm^{-1}$; $\delta_H$ [($CDCl_3$) 0.07(6H, s, ($CH_3$)$_2$Si), 0.87(9H, s, ($CH_3$)$_3$C), 1.35(6H, t, J7.1 Hz, $2 \times CH_2CH_3$), 3.86(2H, d, J8.2 Hz, $CH_2P$), 4.01(4H, m, $CH_2OSi + CH_2OCH_2P$), 4.18(4H, m, $2 \times C\underline{H}_2CH_3$), 4.59(1H, m, CHON); 8.43(1H, s, H-2/H-$\overline{8}$), 8.76(1H, s, H-2/H-8); Found: MH+ 509.1726; $C_{19}H_{34}N_4O_6ClPSi$ requires MH+ 509.1752.

c)

9-(1-t-Butyldimethylsilyloxy-3-diethoxyphosphorylmethoxyprop-2-oxy)adenine

A solution of 9-(1-t-butyldimethylsilyloxy-3-diethoxyphosphorylmethoxyprop-2-oxy)-6-chloropurine (270mg, 0.53 mmol) in ethanolic ammonia (10 ml) was heated in a sealed: metal bomb at 120° C. for 2.5 hours before cooling for 16 hours. The solvent was evaporated, and the residue chromatographed on silica eluting with ethyl acetate-methanol (10:1–5:1)affording 9-(1-t-butyldimethylsilyloxy-3-diethoxyphosphorylmethoxyprop-2-oxy)adenine (182mg, 70%) as a clear gum; $\nu_{max}$ (film) 3320, 1600, 1470, 1250, 1110, 1030, and 970 $cm^{-1}$; $\delta_H$ ($CDCl_3$) 0.07(6H, s, ($CH_3$)$_2$Si), 0.86(9H, s, ($CH_3$)$_3$C), 1.28(6H, t, J7.2 Hz, $2 \times CH_2CH_3$), 3.83(2H, d, J8.2 Hz, $CH_2P$), 3.90(4H, m, $CH_2OSi + C\underline{H}_2OCH_2P$), 4.11(4H, m, $2 \times C\underline{H}_2CH_3$), 4.51(1H, m, $\overline{CHON}$); 5.59(2H, br.s, $D_2O$ exchangeable, $NH_2$), 7.99(1H, s, H-2/H-8); 8.29(1H, s, H-2/H-8), m/z ($NH_3$ C.I.), 490 (MH+, 70%);

DESCRIPTION 10

Intermediates for Examples 21, 22 and 23 a) Diethyl 2.3-bis-(t-butyldimethylsilyloxy)propoxymethylphosphonate

A mixture of diethyl 2,3-dihydroxypropoxymethylphosphonate (2 g, 8.26 mmol), t-butyldimethylchlorosilane (3.llg, 20.66 mmol), imidazole (2.5 g, 36.5 mmol) and 4-dimethylaminopyridine (0.2 g, 1.6 mmol) in N, N-dimethylformamide (25 ml) was stirred at 20° C. for 16 h. The reaction was poured into ethyl acetate (70 ml) and water (70 ml) and the ethyl acetate dried ($Na_2SO_4$). Evaporation in vacuo gave a liquid residue which was chromatographed on silica eluting with ethyl acetate-hexane 2:1, affording diethyl 2,3-bis(t-butyldimethylsilyloxy)propoxymethylphosphonate (3.8 g, 98%) as a clear liquid. $\nu_{max}$ (film) 1460, 1250, 1100 and 1040 $cm^{-1}$; $\delta_H$ ($CDCl_3$) 0.06 (12H, s, $2 \times CH_3SiCH_3$), 0.85 (18H, s, $2 \times (CH_3)_3CSi$), 1.31 (6H, t, J6.9 Hz, $2 \times C\underline{H}_3CH_2$), 3.50 (4H, m, $CH_2OSi + CH_2OCH_2P$), 3.76 (3$\overline{H}$, m, CHOSi + $CH_2P$), 4.13 (4H, m, $2 \times CH_3C\underline{H}_2$).

4 b) Diethyl 2-t-butyldimethylsilyloxy-3-hydroxypropoxymethylphosphonate

A solution of diethyl 2,3-bis(t-butyldimethylsilyloxy)-propoxymethylphosphonate (1 g, 2.13 mmol) in 80% aqueous acetic acid (20 ml) was stirred at 20° C. for 4 h. The solvent was evaporated in vacuo, co-evaporated with toluene and the residue chromatographed on silica, eluting with ethyl acetate-hexane 2:1, affording diethyl 2-t-butyldimethylsilyloxy-3-hydroxypropoxymethylphosphonate (340mg, 45%) as a clear liquid. $\nu_{max}$ (film) 3400, 1460, 1390 and 1250 $cm^{-1}$; $\delta_H$($CDCl_3$), 0.05 (6H, s, $CH_3SiCH_3$), 0.83 (9H, s, ($CH_3$)$_3$CSi), 1.25 (6H, t, J6.9 Hz, $2 \times C\underline{H}_3CH_2$), 2.16 (1H, br.s, $D_2O$ exchangeable, OH), 3.50 (4H, m, $CH_2OH + C\underline{H}_2OCH_2P$), 3.72 (3H, m, CHOSi + $CH_2P$), 4.05 (4H, m, $2 \times CH_3C\underline{H}_2$); m/z (FAB+ve Ion), 357 (MH+).

c)
2-[Bis(t-butoxycarbonyl)amino]-9-(2-tbutyldimethyl- silyloxy -3-diethoxyphosphorylmethoxypropoxy)-6-methoxypurine To a solution of diethyl 2-t-butyldimethylsilyloxy -3-hydroxypropoxymethylphosphate (0.6 g, 1.69 mmol), 2-bis(t-butoxycarbonyl)amino-9-hydroxy-6-methoxypurine (0.64 g, 1.69 mmol) and triphenylphosphine (0.67 g, 2.54 mmol) in dry tetrahydrofuran cooled to 0° C., was added diethyl azodicarboxylate (0.4 g, 2.54 mmol) and stirred at 20° C. under nitrogen for 3 h. The solvents were evaporated in vacuo and the residue chromatographed on silica, eluting with hexane-acetone 2:1, giving 2-[bis(t- butoxycarbonyl)amino]-9-(2-t-butyldimethylsilyloxy-3-diethoxyphosphorylmethoxypropoxy)-6-methoxypurine (0.7 g, 62%) as a clear oil. $\nu_{max}$(film) 1800, 1760, 1600 and 1460 cm$^{-1}$; $\delta_H$(CDCl$_3$) 0.08 (6H, s, CH$_3$SiCH$_3$), 0.85 (9H, s, (CH$_3$)$_3$CSi), 1 33 (6H, t, J6 9 Hz, 2×CH$_3$CH$_2$), 1.45 (18H, s, [(CH$_3$)$_3$COCO]$_2$N), 3.75 (2H, d, J5.2 Hz, CH$_2$OCH$_2$P), 3.86 (2H, d, J8.0 Hz, CH$_2$P), 4.16 (8H, m, 2×CH$_3$CH$_2$3O CHOSi+OCH$_3$), 4.46 (2H, m, CH$_2$ON), 8.12 (1H, s, H-8); m/z (FAB+ve Ion), 742 (MNa+). Found: C, 49.95; H, 7.71; N, 9.71%. C$_{30}$H$_{54}$N$_5$O$_{11}$PSi requires C, 50.06,; H, 7.50; N, 9.73%.

d)
2-Amino-9-[3-(diethoxyphosphorylmethoxy)-2-hydroxypropoxy]-6-methoxyourine A solution of 2-[bis(t-butoxycarbonyl)amino]-9-[2-(t-butyldimethylsilyloxy)-3-(diethoxyphosphorylmethoxy) propoxy]-6-methoxypurine (0.66 g, 0.91 mmol) in 80% acetic acid (25 ml) was stirred at 85° C. for 4 h. The solution was evaporated in vacuo and the residue chromatographed on silica, eluting with chloroformmethanol 25:1, affording 2-amino-9-[3-(diethoxyphosphorylmethoxy)-2-hydroxypropoxy)-6-methoxypurine (275mg, 75%) as a clear gum. $\nu_{max}$ (film) 3460, 3340, 1640, 1580, 1460 and 1390 cm$^{-1}$; $\delta_H$ (CDCl$_3$) 1.34 (6H, t, J6.9 Hz, 2×CH$_3$CH$_2$), 3.75 (2H, m, CH$_2$OCH$_2$P), 3 89 (2H, d, J7.7 Hz, CH$_2$P), 4.04 (1H, m, CHOH), 4.09 (3H, s, OCH$_3$), 4.17 (4H, m, 2×CH$_3$CH$_2$), 4.34 (2H, m, CH$_2$ON), 5.09 (2H, br.s, D$_2$O exchangeable, NH$_2$), 7.78 (1H, s, H-8). Found: C, 40.67; H, 6.18, N, 16.54%; M+ 405.1413. C$_{14}$H$_{24}$N$_5$O$_7$P.0.5H$_2$O requires C, 40.58; H, 6.08; N, 16.90%; M+ 405.1413.

e)
9-[2-(t-Butyldimethylsilyloxy)-3-(diethoxyphosphorylmethoxy)propoxy]-6-phthalimidopurine A mixture of diethyl 2-(t-butyldimethylsilyloxy)-3-(hydroxypropoxymethyl)phosphonate (0.64 g, 1.8 mmol), 9-hydroxy-6-phthalimidopurine (0.51q. 1.8mnol) and triphenylphosphine (0.71q. 2.7 mmol) in tetrahydrofuran was cooled to 0° C. and stirred under nitrogen during the addition of diethyl azodicarboxylate (0.47 g, 2.7 mmol) and then stirred for 3 h at 20° C. The solution was evaporated in vacuo. the residue dissolved in ether, filtered and evaporated in vacuo. The residue was chromatographed on silica, eluting with hexane-acetone 1:1, giving 9-[2-(t-butyldimethylsilyloxy)-3-(diethoxyphosphorylmethoxy)propoxy]-6-phthalimidopurine (1.0 g, 90%) as a pale lemon gum. $\nu_{max}$(film) 3500, 1800, 1740, 1600, 1580 and 1450 cm$^{-1}$; $\delta_H$ (CDCl$_3$) 0.04 (6H,s,CH$_3$SiCH$_3$), 0.76 (9H,s, (CH$_3$)$_3$CSi), 1.21 (6H, t, J6.8 Hz, 2×CH$_3$CH$_2$), 3.65 (2H, d, J5.5 Hz, CH$_2$OCH$_2$P), 3.76 (2H, d, J8.2 Hz CH$_2$P), 4.05 (4H, m, 2×CH$_3$CH$_2$), 4.15 (lH, m, CHOSi CH$_2$ON), 7.80 (4H, m, ArH), 8.23 (1H, s, H-2/H-8), 8.93 (1H, s, H-2/H-8); m/z (FAB+ve Ion), 642 (MNa+), 620 (MH+). Found: C, 51.49; H, 6.28; N, 11.01%; C$_{27}$H$_{38}$N$_5$O$_8$PSi.0.5H$_2$O requires C, 51.58; H, 6.25; N. 11.14%.

f)
9-2-(t-Butyldimethylsilyloxy)-3-(diethoxyphosphorylmethoxy)propoxy]adenine A solution of 9-[2-(t-butyldimethylsilyloxy)-3-(diethoxyphosphorylmethoxy)propoxy]-6-phthalimidopurine (0.99 g, 1.6 mmol) in dichloromethane (10 ml) was cooled to 0° C., treated with methylhydrazine (0.1ml, 1.76 mmol) and stirred at 20° C. for 1.5 h. The reaction mixture was filtered and evaporated in vacuo and the residue dissolved in ether. The ether was filtered, evaporated in vacuo and the residue chromatographed twice on silica, eluting firstly with chloroform-methanol 20:1 and then with chloroform, to give 9-[2-(t -butyldimethylsilyloxy)-3-(diethoxyphosphorylmethoxy)propoxy]adenine (480mg, 61%) as a clear oil. $\nu_{max}$(film) 3350, 1650, 1600 and 1590 cm$^{-1}$; $\delta_H$ (CDCl$_3$) 0.07 (6H, S, CH$_3$SiCH$_3$), 0.88 (9H, S, (CH$_3$)$_3$CSi), 1.34 (6H, t, J6.8 Hz, 2×CH$_3$CH$_2$), 3.75 (2H, d, J5.2 Hz, CH$_2$OCH$_2$P), 3.87 (2H, d, J8.2 Hz, CH$_2$P), 4.17 (4H, m, 2×CH$_3$CH$_2$), 4.22 (1H, m, CHOSi), 4.42 (1H, m, CH$_2$ON), 4.53 (1H, m, CH$_2$ON), 5.71 (2H, br.s, D$_2$O exchangeable, NH$_2$), 7.99 (1H, s, H-2/H-8), 8.36 (1H, s, H-2/H-8). Found: C, 45.57; H, 7.40; N, 13.65%; [M-H]+ 488.0297. C$_{19}$H$_{36}$N$_5$O$_6$PSi.0.7H$_2$O requires C, 45.44; H, 7.50; N, 13.94%; [M-H]+ 488.0294.

DESCRIPTION 11

Intermediates for Examples 24, 25, 26 and 27 a) Diethoxyphosphorylmethoxybut-3-ene

A solution of 3-butene-1-ol (15 g, 208 mmol) in dichloromethane (25 ml) was treated with paraformaldehyde (6.24 g, 208 mmol), cooled in ice and stirred while hydrogen chloride gas was bubbled through until solution occurred. The solution was dried (MgSO$_4$), filtered and evaporated to give residual crude α-chloroether.

The crude c-chloroether was then heated at 140° C. for 2.5 h with triethylphosphite (11.9 ml, 69.3 mmol) and stirred at 20° C. for 16 h. The reaction mixture was diluted with chloroform, washed with saturated sodium hydrogen carbonate solution, dried (MgSO$_4$) and evaporated. The residue was chromatographed on silica eluting with hexane-acetone (1:1) affording diethoxyphosphorylmethoxybut-3-ene (8.8 g, 19%) as a clear liquid. $\nu_{max}$ (film) 3500, 1650, 1480, 1450 and 1400 cm$^{-1}$; $\delta_H$ (CDCl$_3$) 1.35 (6H, t, J6.9 Hz, 2×CH$_2$CH$_3$), 2.36 (2H, m, CHCH$_2$), 3.63, (2H, t, J6.8 Hz, CH$_2$OCH$_2$P), 3.79 (2H, d, J8.5 Hz, CH$_2$P), 4.17 (4H, m, 2×CH$_2$CH$_3$), 5.07 (2H, m, CH=CH$_2$) and 5.81 (1H, m, CH=CH$_2$). Found: C, 47.59; H, 8.72%; C$_9$H$_{19}$O$_4$P.0.2-H$_2$O requires C, 47.86; H, 8.66%.

b) Diethyl 3,4-dihydroxybutoxymethylphosphonate

A solution of diethoxyphosphorylmethoxybut-3-ene (8.8. g, 39.6 mmol) in acetone-water (1:1, 150 ml) was treated with N-methylmorpholine-N-oxide monohydrate (8.56 g, 63.4 mmol) and osmium tetroxide (2 crystals).

The reaction mixture was stirred for 6 days at 20° C., before evaporating the solution in vacuo and chromatographing the residue on silica, eluting with chloroform-methanol 10:1, affording diethyl 3,4-dihydroxybutoxymethylphosphonate (8.42 g, 83%) as a clear oil. $\nu_{max}$ (film) 3400, 1480, 1440 and 1400 cm$^{-1}$; $\delta_H$(CDCl$_3$) 1.24 (6H, t, J6.8 Hz, 2×CH$_2$CH$_3$), 1.43 (1H, m, CH$_2$CHOH), 1.69 (1H, m, CH$_2$CHOH), 3.26 (2H, m, CH$_2$OH), 3.49 (1H, m, CHOH), 3.58 (2H, m, CH$_2$OCH$_2$P), 3.76 (2H, d, J8.3 Hz, CH$_2$P), 4.04 (4H, m, 2×CH$_2$CH$_3$), 4.46 (2H, m, D$_2$O exchangeable, 2×OH). Found: C, 40.64; H, 8.35%; C$_9$H$_{21}$O$_6$P.0.5H$_2$O requires C, 40.75; H, 8.36%.

C) Diethyl 4-t-butyldimethy]si]y]OXy-3hydroxybutoxymethylphosphonate

A mixture of diethyl 3,4-dihydroxybut-2-oxymethylphosphonate (8.27 g, 32.3 mmol), triethylamine (4.95 ml, 35.5 mmol), t-butyldimethylchorosilane (5.84 g, 38.76 mmol) and 4-dimethylaminopyridine (0.16 g, 1.3 mmol) in dichloromethane (100 ml) was stirred at 20° C. for 24 h. The solution was washed with water (2×80 ml), dried (MgSO$_4$) and evaporated under vacuum to give diethyl 4-t-butyldimethylsilyloxy-3-hydroxybutoxymethylphosphonate (9.0 g, 75%) as a yellow oil. $\nu_{max}$(film) 3400, 1470, 1440 and 1390 cm$^{-1}$; $\delta_H$(CDCl$_3$) 0.04 (6H, s, Si(CH$_3$)$_2$), 0.86 (9H, s, (CH$_3$)$_3$CSi), 1.23 (6H, t, J6.8 Hz, 2×CH$_2$CH$_3$), 1.43 (1H, m, CH$_2$CHOH), 1.75 (1H, m, CH$_2$CHOH), 3.38 (1H, m, CHOH), 3.49 (2H, m, CH$_2$OSi), 3.59 (2H, m, CH$_2$OCH$_2$P), 3.75 (2H, d, J8.2 Hz, CH$_2$OCH$_2$P), 4.04 (4H, m, 2×CH$_2$CH$_3$), 4.51 (1H, d, J5.0 Hz, D$_2$O exchangeable, OH). Found: C, 48.23; H, 9.82%; MH$^+$ 371.2032 C$_{15}$H$_{35}$O$_6$PSi requires C, 48.63; H, 9.52%; MH$^+$ 371.2019.

d) 2-Bis(t-butoxycarbonvl)amino1-9-[1-(t-butyldimethylsilyloxy)-4-(diethoxyphosphorylmethoxy)-but-2-oxy1-6-methoxypurine A solution of diethyl 4-t-butyldimethylsilyloxy -3-hydroxybutoxymethylphosphonate (0.49 g, 1.31 mmol), 2-[bis(t-butoxycarbonylamino]-9-hydroxy-6-methoxypurine (0.5 g, 1.31 mmol) and triphenylphosphine (0.52 g, 19.7 mmol) in tetrahydrofuran (50 ml) was cooled to 0° C. and treated with diethyl azodicarboxylate (0.31 ml, 1.97 mmol) before stirring for 4 h at 20° C. under nitrogen. The solution was evaporated in vacuo and the residue chromatographed twice on silica, eluting with chloroform-methanol 100:1 and then dichloromethanemethanol 200:1, affording 2-[bis(t-butoxycarbonyl)amino]-9-[1-(t-butyldimethylsilyloxy)-4-(diethoxyphosphorylmethoxy)but-2-oxy]-6-methoxypurine (0.45 g, 47%) as a clear oil. $\nu_{max}$(film) 3450, 1790, 1750, 1600, 1470, 1440 and 1390 cm$^{-1}$; $\delta_H$(CDCl$_3$) 0.05 (6H, s, Si(CH$_3$)2), 0.83 (9H, s, (CH$_3$)$_3$CSi), 1.27 (6H, t, J6.9 Hz, 2×CH$_2$CH$_3$), 1.40 (18H, s, 2×(CH$_3$)$_3$CN), 2.01 (2H, m, PCH$_2$OCH$_2$CH$_2$), 3.74 (6H, m, CH$_2$OCH$_2$P+CH$_2$0Si), 4.09 (7H, m, 2×CH$_2$CH$_3$+OCH$_3$), 4.50 (1H, m, CHCH$_2$Si), 8.10 (1H, s, H-8). Found: C, 50.54; H, 7.66; N, 9.38%; C$_{31}$H$_{56}$N$_5$O$_{11}$PSi requires C, 50.74; H, 7.69; N, 9.54%.

e) 9-1-(t-Butyldimethylsilyloxy)-4-(diethoxyohosphorylmethoxy)but-2-oxy1-6-phthalimidopurine A solution of diethyl 4-t-butyldimethylsilyloxy-3-hydroxybutoxymethylphosphonate (0.49 g, 1.31 mmol), 9-hydroxy-6-phthalimidopurine (0.5 g, 1.31 mmol) and triphenylphosphine (0.52 g, 1.97 mmol) in dry tetrahydrofuran (50 ml) was stirred under nitrogen at 0° C. during the addition of diethyl azodicarboxylate (0.31 ml, 1.97 mmol). The solution was then stirred at 20° C for 4 h and evaporated in vacuo. The residue was chromatographed on silica, eluting with hexane-acetone 4:1 affording 9-[1-(t-butyldimethylsilyloxy)-4-(diethoxyphosphorylmethoxy)but-2-oxy]-6-phthalimidopurine (575mg, 69%) as a clear oil. $\nu_{max}$(film) 3500, 1790, 1740 1600 and 1580 cm$^{-1}$; $\delta_H$ [(CD$_3$)$_2$SO] 0.04 (6H, s CH$_3$SiCH$_3$), 0.74 (9H, s, (CH$_3$)$_3$CSi), 1.22 (6H, t, J6.9 Hz, 2×CH$_3$CH$_2$), 2.04 (2H, m, SiOCH$_2$CHCH$_2$), 3.79 (2H, m, CH$_2$OSi), 3.88 (2H, d, J8.2 Hz, CH$_2$P), 3.96 (2H, m, CH$_2$OCH$_2$P), 4.03 (4H, m, 2×CH$_3$CH$_2$), 4.69 (1H, m, CHON), 8.05 (4H, m, ArH), 8.91 (1H, s, H-2/H-8), 9.07 (1H, s, H-2/H-8); m/z (FAB+ve Ion), 656 (MNa$^+$) and 634 (MH$^+$). Found: C, 53.10 H, 6.30; N, 10.83%; C$_{28}$H$_{40}$N$_5$O$_8$PSi requires C, 53.07; H, 6.36,; N, 11.05%.

f) 9-[1-(t-Butyldimethylsilyloxy)-4-(diethoxyphosphorylmethoxy)but-2-oxy]adenine A solution of 9-[1-(t-butyldimethylsilyloxy)-4-(diethoxyphosphorylmethoxy)but-2-oxy]-6-phthalimidopurine (550 mg, 0.87 mmol) in dichloromethane (10 ml) was treated with methylhydrazine (0.05 ml, 0.96 mmol) and stirred for 30 min at 20° C. The reaction mixture was filtered, the solvent evaporated in vacuo and the residue chromatographed on silica, eluting with chloroform-methanol 40:1, affording 9-[1-(t-butyldimethylsilyloxy)-4-(diethoxyphosphorylmethoxy)-but-2-oxy]adenine (380mg, 87%) as a clear oil. $\nu_{max}$ (film) 3340, 3200, 1730, 1650, 1600 and 1470 cm$^{-1}$, $\delta_H$ (CDCl$_3$) 0.04 (6H, s, CH$_3$SiCH$_3$), 0.87 (9H, s, (CH$_3$)$_3$CSi), 1.33 (6H, t, J7.1 Hz, 2×CH$_3$CH$_2$), 2.08 (2H, m, SiOCH$_2$CHCH$_2$), 3.80-3.90 (4H, m, CH$_2$O-Si+CH$_2$P), 3.99 (2H, m, CH$_2$OCH$_2$P), 4.16 (4H, m, 2×CH$_3$CH$_2$), 4.61 (1H, m, CHON), 5.68 (2H, br.s, D$_2$O exchangeable, NH$_2$), 8.04 (1H, s, H-2/H-8), 8.34 (1H, s, H-2/H-8); m/z (FAB+ve Ion), 526 (MNa$^+$), 504 (MH$^+$); Found: C, 47.35; H, 7.68; N, 13.67% C$_{20}$H$_{38}$N$_5$O$_6$PSi requires C, 47.50; H, 7.60; N, 13.91%.

EXAMPLE 1

9-[3-(Diethoxyphosphorylmethoxy)propoxy]guanine

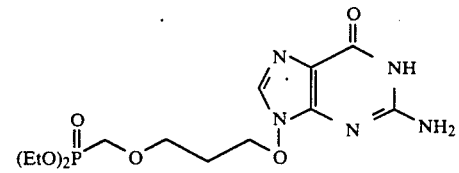

6-Chloro-9-[3-(diethoxyphosphorylmethoxy)propoxy]-2-formamidopurine (1.5 g, 3.56 mmol) was heated at 100° C. for 2 h in 80% formic acid (15 ml) then evaporated under reduced pressure. The residue was taken up in methanol (15 ml) and 0.88 ammonia (15 ml) and stirred at 25° C. for 1 h then evaporated to dryness. Precipitation from hot water afforded 9-[3-(diethoxyphosphorylmethoxy)propoxy]guanine (0.69 g, 52%) as a pale yellow solid; $\nu_{max}$ 3335, 1694, 1475, 1390, 1249, 1026 cm$^{-1}$; $\delta_H$[(CD$_3$)$_2$SO] 1.22(6H, t, J7 Hz, (CH$_3$CH$_2$O)$_2$), 1.90(2H, m, CH$_2$CH$_2$CH$_2$), 3.68(2H, t, J6 Hz, CH$_2$OCH$_2$P), 3.83(2H, d, J8.3 Hz, CH$_2$P), 4.03(4H, m, (CH$_3$CH$_2$O)$_2$), 4.31(2H, t, J6.6 Hz, CH$_2$ON), 6.60(2H, br.s, D$_2$O exchangeable, NH$_2$) 7.95(1H, s, H-8), 10.50(1H, br.s, D$_2$O exchangeable,

EXAMPLE 2

9-[3-(Phosphonomethoxy)propoxy]guanine

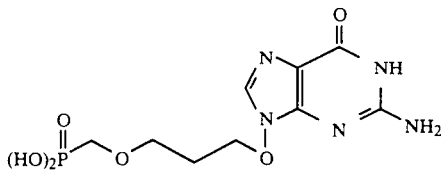

Bromotrimethylsilane (0.79 ml, 6 mmol) was added dropwise to a solution of 9-[3-(diethoxyphosphorylmethoxy)propoxy]guanine (0.38 g, 1 mmol) in dry N,N-dimethylformamide (4 ml) and the reaction stirred under nitrogen at 25° C. for 2 h. Concentration in vacuo, followed by co-evaporation three times with methanol gave an off-white solid which on recrystallisation from hot water gave 9-[3-(phosphonomethoxy)propoxy]guanine (267 mg, 83%) as a white crystalline solid; m.p. 247°-250° C.; $\nu_{max}$(KBr) 3320, 1693, 1646, 1370, 1250 cm$^{-1}$; $\delta_H$[(CD$_3$)$_2$SO] 1.90(2H, m, CH$_2$CH$_2$CH$_2$), 3.57(2H, d, J8.5 Hz, CH$_2$P), 3.67(2H, t, J6 Hz, CH$_2$OCH$_2$P), 4.32(2H, t, J6.6 Hz, NOCH$_2$), 6.60(2H, br.s, D$_2$O exchangeable, NH$_2$), 7.95(1H, s, H-8), 10.63(1H, br.s, D$_2$O exchangeable, NH); Found: C, 33.84; H, 4.60; N, 21.57%; C$_9$H$_{14}$N$_5$O$_6$P requires: C, 33.86; H, 4.42; N, 21.94%.

EXAMPLE 3

2,6-Diamino-9-[3-(diethoxyphosphorylmethoxy)-propoxy]purine

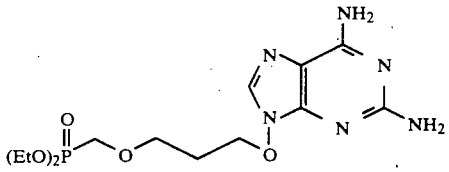

A solution of 6-chloro-9-[3-(diethoxyphosphorylmethoxy)propoxy]-2-formamidopurine (1.2 g, 2.85 mmol) in ethanolic ammonia (25 ml) was heated at 110° C. in an autoclave for 7.5 h then left to cool for 12 h. The reaction was then evaporated in vacuo and the residue chromatographed on silica eluting with chloroform/methanol (10:1) to give 2,6-diamino-9-[3-(diethoxyphosphorylmethoxy)propoxy]purine as a pale yellow solid (0.34 g, 32%); $\nu_{max}$(KBr) 3313, 3149, 1586, 1481, 1240, 1054 cm$^{-1}$; $\delta_H$[(CD$_3$)$_2$SO] 1.22(6H, t, J7 Hz,(CH$_3$CH$_2$O)$_2$), 1.91(2H, m, CH$_2$CH$_2$CH$_2$), 3.70(2H, t, J6 Hz, CH$_2$OCH$_2$P), 3.84(2H, d, J7.98 Hz,CH$_2$P), 4.04(4H, m,(CH$_3$CH$_2$O)$_2$), 4.31(2H, t, J6.5 Hz, NOCH$_2$), 5.93(2H, br.s, D$_2$O exchangeable, NH$_2$), 6.77(2H, br.s, D$_2$O exchangeable, NH$_2$), 7.94(1H, s, H-8); Found C, 41.25; H, 6.32; N, 22.65%; M+ 374.1477; C$_{13}$H$_{23}$N$_6$O$_5$P.0.2H$_2$O requires: C, 41 31; H, 6.35; N, 22.24%; M+ 374.1468.

NH); Found C, 41.90; H, 5.94; N, 18.65%; C$_{13}$H$_{22}$N$_5$O$_6$P requires: C, 41.60; H, 5 91; N, 18.61%.

EXAMPLE 4

2,6-Diamino-9-[3-(phosphonomethoxy)propoxy]purine

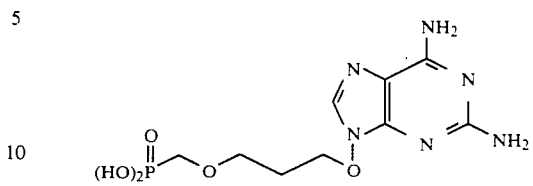

Bromotrimethylsilane (1.12 ml, 8.5 mmol) was added dropwise to a solution of 2,6-diamino-9-[3-(diethoxyphosphorylmethoxy)propoxy]purine (0.32 g, 0.85 mmol) in dry N,N-dimethylformamide (2 ml) and the reaction stirred under nitrogen at 25° C. for 2 h. After concentration in vacuo the residue was co-evaporated twice with methanol then filtered from hot methanol/water to give 2,4-diamino-9-[3-(phosphonomethoxy)propoxy]purine (183 mg, 68%) as an off-white amorphous solid; $\nu_{max}$(KBr) 3381, 3105, 1660, 1591, 1408, 1125, 1041 cm$^{-1}$; $\delta_H$(TFA-d$_1$+d$_6$-Acetone) 2.26(2H, t, J6 Hz, CH$_2$CH$_2$CH$_2$), 4.01(2H, t, J5.6 Hz, CH$_2$OCH$_2$P), 4.16(2H, d, J8.5 Hz, CH$_2$P), 4.75(2H, t, J6 Hz, CH$_2$ON), 9.04(1H, s, H-8); Found C, 33.49; H, 4.83; N, 25.81%; C$_9$H$_{15}$N$_6$O$_5$P.0.25H$_2$O requires: C, 33.49; H, 4.84; N, 26.04%.

EXAMPLE 5

9-[3-(Diethoxyphosphorylmethoxy)propoxy]adenine

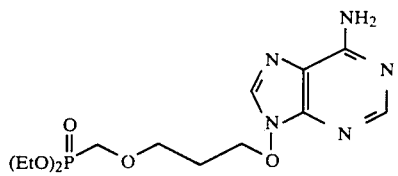

6-Chloro-9-[3-(diethoxyphosphorylmethoxy)propoxy]purine (0.75 g, 1.98 mmol) was dissolved in ethanolic ammonia (20 ml) and heated at 110° C. in an autoclave for 7.5 h then cooled for 13 h. The reaction was then evaporated to dryness under reduced pressure and chromatographed in chloroform/methanol (30:1) to give 9-[3-(diethoxyphosphorylmethoxy)propoxy]adenine (270 mg, 38%) as a white solid; $\nu_{max}$(KBr) 3378, 3335, 3186, 1660, 1598, 1230, 1019 cm$^{-1}$; $\delta_H$[(CD$_3$)$_2$SO] 1.22(6H, t, J7 Hz, (CH$_3$CH$_2$O)$_2$), 1.94(2H, m, CH$_2$CH$_2$CH$_2$), 3.74(2H, t, J6 Hz, CH$_2$OCH$_2$P), 3.83(2H, d, J8.3 Hz, CH$_2$P), 4.04(4H, m, (CH$_3$CH$_2$O)$_2$), 4.42(2H, t, NOCH$_2$), 7.37(2H, br.s, D$_2$O exchangeable, NH$_2$), 8.14 and 8.42(2H, 2s, H-2 and H-8); Found: C, 43.63; H, 6.15; N, 19.78%; M+ 359.1350; C$_{13}$H$_{22}$N$_5$O$_5$P requires: C, 43.45; H, 6.17; N, 19.49%; M+ 359.1359.

EXAMPLE 6

9-[3-(Phosphonomethoxy)propoxy]adenine

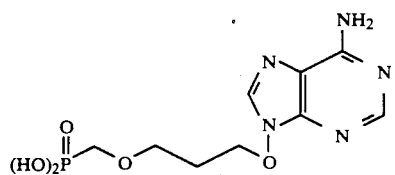

Bromotrimethylsilane (0.55 ml, 4.18 mmol) was added dropwise to a solution of 9-[3-(diethoxyphosphorylmethoxy)propoxy]adenine (0.25 g, 0.70 mmol) in dry dichloromethane (2 ml) and the reaction stirred under nitrogen at 25° C. for 3 h. After concentration in vacuo the residue was co-evaporated three times with methanol. Reverse-phase chromatography, eluting with 5% aqueous methanol gave 9-[3-(phosphonomethoxy)propoxy]adenine (152 mg, 71%) as a white solid; m.p. 246°–249° C. $v_{max}$(KBr) 3320, 3084, 1700, 1079 cm$^{-1}$; $\delta_H$[(CD$_3$)$_2$SO] 1.94(2H, t, J6.3 Hz, CH$_2$CH$_2$CH$_2$), 3.56(2H, d, J8.5 Hz, CH$_2$P), 3.70(2H, t, J6 Hz, CH$_2$OCH$_2$P), 4.43(2H, t, J6 Hz, NOCH$_2$), 7.40(2H, br s, D$_2$O exchangeable, NH$_2$), 8.15(1H, s, H-2), 8.43(1H, s, H-8); Found: C, 34.15; H, 5.12; N, 21.89%; C$_9$H$_{14}$N$_5$O$_5$P.0.8H$_2$O requires: C, 34.03; H, 4.95; N, 22.04%.

EXAMPLE 7

9-[3-(Ethoxy(hydroxy)phosphorylmethoxy)propoxy]-guanine

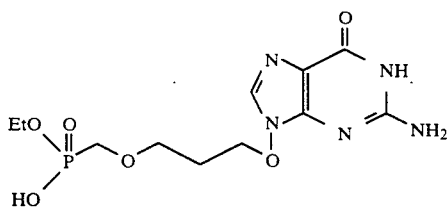

9-[3-(Diethoxyphosphorylmethoxy)propoxy]guanine (0.26 g, 0.69 mmol) was heated under reflux for 3 hours sodium hydroxide (5 ml), cooled and brought to pH 2.0 with 5M hydrochloric acid. After evaporation to dryness, the residue was purified by reverse-phase chromatography in aqueous methanol to give 9-[3-(ethoxy(hydroxy)phosphorylmethoxy)propoxy]guanine (27 mg, 11%) as a white solid; m.p. 166°–175° C.; $v_{max}$ (KBr) 1693, 1646, 1595, 1477 cm$^{-1}$; $\delta_H$[(CD$_3$)$_2$SO] 1.19(3H, t, J7.15 Hz, (CH$_3$CH$_2$O)$_2$), 1.90(2H, m, CH$_2$CH$_2$CH$_2$), 3.66(2H, m, CH$_2$OCH$_2$P), 3.67(2, d, J8.52 Hz, CH$_2$P), 3.96(2H, m, CH$_3$CH$_2$O), 4.31(2H, t, J6.6 Hz, CHON), 6.60(2H, br s, D$_2$O exchangeable NH$_2$), 7.95(1H, s, H-8), 10.64(1H, br s, D$_2$O exchangeable, NH); Found: C, 36.85; H, 5.24; N, 19.19%; C$_{11}$H$_{18}$N$_5$O$_6$P.0.6H$_2$O requires: C, 36.90; H, 5.40; N, 19.56%; m/z(FAB+ve ion) MH+ 348.

EXAMPLE 8

2,6-Diamino-9-[(3-diethoxyphosphorylmethoxy-2-hydroxymethyl)propoxy]purine

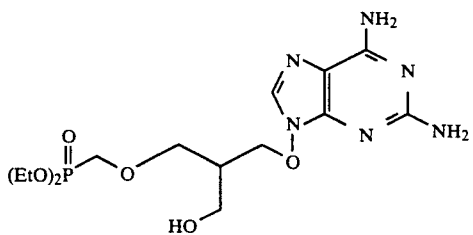

A solution of 9-[(2-acetoxymethyl-3-diethoxyphosphorylmethoxy)propoxy]-6-chloro-2-formamidopurine (1.0 g, 2.0 mmol) in ethanolic ammonia (20 ml) was heated at 110° C. in a bomb for 4 h then left to cool for 12 h. The reaction was then evaporated in vacuo and the residue dissolved in ethanol (15 ml) and refluxed for 2.5 h with 5MHCl (0.4 ml). After taking the solution to pH8.0 with 0.88NH$_3$, the reaction was evaporated to dryness and the residue recrystallised from ethanol to give 2,6-diamino-9-[(3-diethoxyphosphorylmethoxy-2-hydroxymethyl)-propoxy]purine as an off-white solid (0.26 g, 32%). $v_{max}$ (KBr) 3331, 3175, 1586, 1486, 1407, 1241, 1050 cm$^{-1}$; $\delta_H$[(CD$_3$)$_2$SO] 1.32(6H, t, J7 Hz, (CH$_3$CH$_2$O)$_2$), 2.21(1H, m, CH), 3.62(2H, m, CH$_2$), 3.76(2H, d, J5.8 Hz, CH$_2$), 3.95(2H, d, J7.97 Hz, CH$_2$P), 4.13(4H, m, (CH$_3$CH$_2$O)$_2$), 4.36(2H, m, CH$_2$), 4.82(1H, t, J5. Hz, D$_2$O exchangeable, OH), 6.01(2H, br s, D$_2$O exchangeable, NH$_2$), 6.87(2H, br s, D$_2$O exchangeable, NH$_2$); 8.04(1H, s, H-8); Found: C, 41.02; H, 6.31; N, 20.45%; C$_{14}$H$_{25}$N$_6$O$_6$P.0.3H$_2$O requires: C, 41.04; H, 6.30; N, 20.51%; m/z 404(M+, 5%).

EXAMPLE 9

2,6-Diamino-9-[(2-hydroxymethyl-3-phosphonomethoxy)propoxy]purine

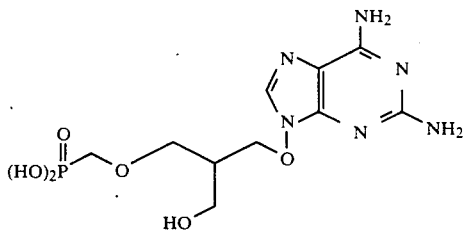

Bromotrimethylsilane (0.71 ml, 5.4 mmol) was added dropwise to a solution of 2,6-diamino-9-[(3-diethoxyphosphorylmethoxy-2-hydroxymethyl)propoxy]purine (0.22 g, 0.54 mmol) in dry N,N-dimethylformamide (2 ml) and the reaction stirred under nitrogen at 25° C. for 2 h. After concentration in vacuo the residue was co-evaporated three times with methanol before addition of water (3 ml) and filtration afforded 2,6-diamino-9-[(2-hydroxymethyl-3-phosphonomethoxy)propoxy]purine as an off-white solid (147 mg, 78%) $v_{max}$ (KBr) 3326, 3159, 1675, 1409, 1048 cm$^{-1}$; $\delta_H$[(CD$_3$)$_2$SO+NH$_3$] 2.04(1H, m, CH), 3.34(2H, CH$_2$), 3.54(2H, d, J5.0 Hz, CH$_2$), 3.63(2H, m, CH$_2$), 4.24(2H, d, J6.1 Hz, CH$_2$), 6.10(2H, br s, D$_2$O exchangeable, NH$_2$), 6.80(2H, br s, D$_2$O exchangeable, NH$_2$), 7.95(1H, s, H-8); Found C, 33.10; H, 4.84; N, 23.25%; C$_{10}$H$_{17}$N$_6$O$_6$P.0.7H$_2$O requires: C, 33.28; H, 5.14; N, 23.29%; m/z (FAB+ve ion, thioglycerol) MH+ 349.

EXAMPLE 10

9-[(3-Diethoxyphosphorylmethoxy-2-hydroxymethyl)-propoxy]guanine

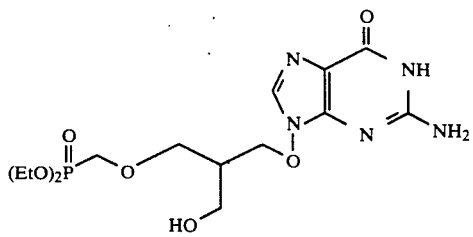

9-[2-Acetoxymethyl-3-diethoxyphosphorylmethoxy)propoxy]-6-chloro-2-formamidopurine (0.93 g, 1.88 mmol) was heated at 100° C. for 1.5 h in 80% formic acid (10 ml) then evaporated under reduced pressure. The residue was taken up in methanol (5 ml) and 0.88 ammonia (5 ml) and stirred at 25° C. for 2 h then evaporated to dryness. The residue was dissolved in ethanol (15 ml) and 5M HCl (0.38 ml, 1.88 mmol) and heated under reflux until deacylation was complete. The reaction mixture was adjusted to pH 8.0 with 0.88 ammonia and then reduced. Reverse-phase chromatography eluting with aqueous methanol gave 9-[(3-diethoxyphosphorylmethoxy-2-hydroxymethyl)propoxy]guanine as a pale yellow solid (0.20 g, 26%); m.p. 123°–128° C.; $v_{max}$ (KBr) 1692, 1475, 1242, 1054, 1026 cm$^{-1}$; $\delta_H[(CD_3)_2SO]$ 1.22(6H, t, J7.15 Hz, (CH$_3$CH$_2$O)$_2$), 2.10(1H, m, CH), 3.52(2H, m, CH$_2$OH), 3.66(2H, d, J6.05 Hz, CH$_2$OCH$_2$P), 3.83(2H, d, J7.97 Hz, CH$_2$P), 4.03(4H, m, (CH$_3$CH$_2$O)$_2$), 4.27(2H, m, CH$_2$ON), 6.58(2H, br s, D$_2$O exchangeable, NH$_2$), 7.95(1H, s, H-8), 10.64(1H, br s, D$_2$O exchangeable, NH); Found: C, 39.45; H, 5.99; N, 17.06%; C$_{14}$H$_{24}$N$_5$O$_7$P.0.9H$_2$O requires: C, 39.89, H, 6.18; N, 16.61%; m/z (FAB+ve ion) MH+ 406.

EXAMPLE 11

9-[(2-Hydroxymethyl-3-phosphonomethoxy)propoxy]guanine

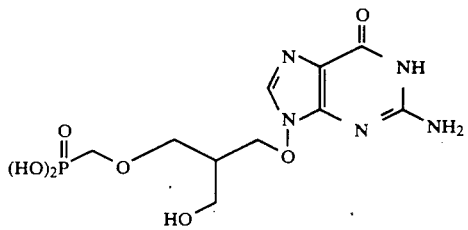

A solution of 9-[(3-diethoxyphosphorylmethoxy-2-hydroxymethyl)propoxy]guanine (100 mg, 0.25 mmol) in dry N,N-dimethylformamide (1ml) was stirred at 25° C. under nitrogen with bromotrimetylsilane (0.2 ml, 1.5 mmol) for 9 h. The reaction mixture was then reduced and coevaporated twice with methanol before reverse-phase chromatography in water to give 9-[(2-hydroxymethyl-3-phosphonomethoxy)propoxy]guanine (44 mg, 51%). The sample was freeze-dried from water to give a white amorphous solid. $v_{max}$ (KBr) 3394, 1700, 1645, 1600, 1476, 1385, 1164 cm$^{-1}$; $\delta_H[(CD_3)_2SO]$ 2.10(1H, m, CH), 3.53(2H, m, CH$_2$OH), 3.57(2H, d, J8.52 Hz, CH$_2$P), 3.64(2H, d, J6.05 Hz, CH$_2$OCH$_2$P), 4.28(2H, m, CH$_2$ON), 6.61(2H, br s, D$_2$O exchangeable, NH$_2$), 7.95(1H, s, H-8), 10.63(1H, br s, D$_2$O exchangeable, NH); Found: C, 33.94; H, 4.75; N, 19.93%; C$_{10}$H$_{16}$N$_5$O$_7$P .0.2H$_2$O requires: C, 34.04; H, 4.69; N, 19.85%; m/z (FAB+ve ion) MH+392.

EXAMPLE 12

9-[(3-Diethoxyphosphorylmethoxy-2-hydroxymethyl)propoxy]adenine

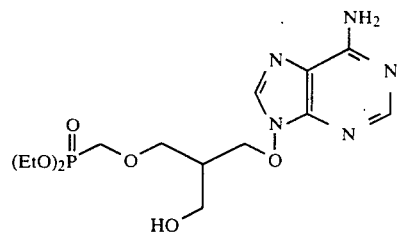

9-[(2-Acetoxymethyl-3-diethoxyphosphorylmethoxy)propoxy]-6-chloropurine (590 mg, 1.3 mmol) was dissolved in ethanolic ammonia (10 ml) and heated at 110° C. in a bomb for 4 h then cooled for 11 h. The reaction mixture was then evaporated to dryness under reduced pressure and the residue refluxed in ethanol (5 ml) with 5M HCl (0.26 ml) for 6 h. On cooling, the reaction mixture was adjusted to pH8.0 with 0.88 ammonia, reduced and the residue chromato-graphed on reverse-phase silica with aqueous methanol to give 9-[(3-diethoxyphosphorylmethoxy-2-hydroxymethyl)propoxy]adenine as a yellow oil (110 mg, 22%); $v_{max}$ 3330, 1660, 1600, 1480, 1230, 1030 cm$^{-1}$; $\delta_H[(CD_3)_2SO]$ 1.21(6H, t, J7 Hz, (CH$_3$CH$_2$O)$_2$), 2.15(1H, m, CH), 3.56(2H, m, CH$_2$OH), 3.68(2H, m, CH$_2$OCH$_2$P), 3.83(2H, d, J8.25 Hz, CH$_2$P), 4.03(4H, m, (CH$_3$CH$_2$O)$_2$), 4.38(2H, m, CH$_2$ON), 4.72(1H, t, J5.3 Hz, D$_2$O exchangeable, OH), 7.38(2H, br s, D$_2$O exchangeable, NH$_2$), 8.14 and 8.42(2×1H, 2×s, H-8 and H-2); Found: MH+ 389.1454; C$_{14}$H$_{24}$N$_5$O$_6$P requires: 389.1464.

EXAMPLE 13

9-[(2-Hydroxymethyl-3-phosphonomethoxypropoxy]adenine

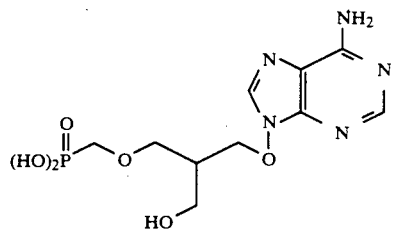

A solution of 9-[3-diethoxyphosphorylmethoxy-2-hydroxymethyl)propoxy]adenine (100 mg, 0.22 mmol) in dry N,N-dimethylformamide (2 ml) was stirred at 25° C. under nitrogen with bromotrimethylsilane (0.29 ml, 2.2 mmol) for 3 h. The reaction mixture was then reduced and coevaporated twice with methanol before reverse-phase chromatography to give 9-[(2-hydroxymethyl-3-phosphonomethoxy)propoxy]adenine (33 mg, 45%) as a white solid; m.p 220°–222° C.; $v_{max}$(KBr) 3380, 3220, 1700 and 1080 cm$^{-1}$; $\delta_H[(CD_3)_2SO]$ 2.15(1H, m, CH); 3.57(2H, m, CH$_2$OH); 3.57(2H, d, J8.25 Hz, CH$_2$P); 3.68(2H, d, J6.0 Hz, CH$_2$OCH$_2$P); 4.39(2H, m, CH$_2$ON); 7.64(2H, br s, D$_2$O exchangeable, NH$_2$); 8.20 and 8.49(2×1H, 2×S, H-8 and H-2); Found: C, 34.27; H, 5.09; N, 19.79% C$_{10}$H$_{16}$N$_5$O$_6$P.1.0 H$_2$O requires C, 34.19; H, 5.16; N, 19.94%. m/z(FAB+ve ion) MH+334 (65%).

EXAMPLE 14

9-[(3-Ethoxy(hydroxy)phosphorylmethoxy-2-hydroxymethyl)propoxy]guanine

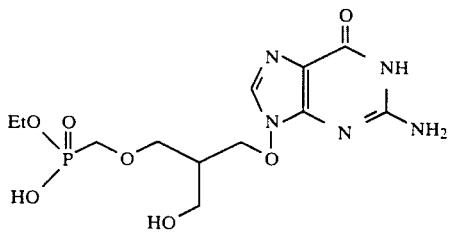

9-[(3-Diethoxyphosphorylmethoxy-2-hydroxymethyl)propoxy]guanine (32 mg, 0.08 mmol) was heated under reflux for 2 h in 10% sodium hydroxide (3 ml), cooled and brought to pH 2.0 with 5M hydrochloric acid. After evaporation to dryness, the residue was purified by reverse-phase chromatography in water to give 9-[(3-ethoxy(hydroxy)phosphorylmethoxy-2-hydroxymethyl)propoxy]guanine as a white solid. (15 mg, 50%) m.p. 150°–154° C.; $\nu_{max}$(KBr) 3420, 1695, 1610, 1480, 1380, 1050 cm$^{-1}$; $\delta_H$[(CD$_3$)$_2$SO] 1.18(3H, t, J 7 Hz. CH$_3$CH$_2$O); 2.10(1H, m, CH); 3.52(2H, dd, J 5.6, 2 Hz); 3.65(4H, m, CH$_2$OCH$_2$P); 3.93(2H, m, CH$_3$CH$_2$O); 4.27(2H, m, CH$_2$ON); 6.63(2H, br.s D$_2$O exchangeable, NH$_2$); 7.95(1H, s, H-8); 10.67(1H, br.s, D$_2$O exchangeable, NH); m/z(FAB+ve ion) MH+ 378 (53%); Found: C, 35.90; H, 5.78; N, 17.42% C$_{12}$H$_{20}$N$_5$O$_7$P.1.5H$_2$O requires C, 35.64; H, 5.69; N, 17.33%.

EXAMPLE 15

9-(1-Diethoxyphosphorylmethoxy-3-hydroxyprop-2-oxy)guanine

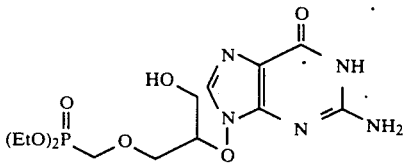

A solution of 9-(1-t-butyldimethylsilyloxy-3-diethoxyphosphorylmethoxyprop-2-oxy)-6-chloro-2-formamidopurine (280 mg, 0.51 mmol) in 80% aqueous formic acid (5 ml) was stirred at 120° C. for 3 hours. The acid was evaporated, the residue dissolved in methanol (1 ml) and 0.88 ammonia (1 ml) and stirred for 1 hour at 20° C. After evaporation, the residue was dissolved in hot water (5 ml) and extracted with ether (3×5 ml). The aqueous solution was passed down a reverse-phase silica column eluting with up to 15% methanol affording 9-(1-diethoxyphosphorylmethoxy-3-hydroxyprop-2-oxy)guanine (105 mg, 53%) m.p. 238°–240° C. $\nu_{max}$ (KBr) 3380, 1700, 1600, 1380, 1380, 1240, 1030 and 960 cm$^{-1}$; $\delta_H$[(CD$_3$)$_2$SO] 1.24(6H, t, J7.2 Hz, 2×(CH$_2$CH$_3$), 3.61(2H, t, J5.2 Hz, CH$_2$OH), 3.81(2H, d, J4.7 Hz, CH$_2$OCH$_2$P), 3.89(2H. d, J8.0 Hz,CH$_2$P), 4.04 (4H, m, 2×CH$_2$CH$_3$, 4.39(1H, t, J4.7 Hz,CHON), 5.06(1H, t, J6.0 Hz, D$_2$O exchangeable, OH), 6.61(2H, br.s, D$_2$O exchangeable, NH$_2$), 7.86(1H, s, H-8), 10.67(1H, br.s, D$_2$O exchangeable, NH); m/z (FAB+veIon), 392(MH+, 2%), 414(MNa+, 100%).

Found: C,39.27; H,5.60; N,17.78%; C$_{13}$H$_{22}$N$_5$O$_7$P.0.3-H$_2$O requires C,39.36; H,5.74; N,17.66%.

EXAMPLE 16

9-(1-Hydroxy-3-phosphonomethoxyprop-2-oxy)guanine

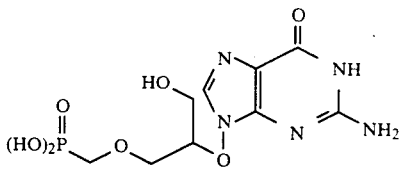

Bromotrimethylsilane (290 mg, 0.25 ml, 1.9 mmol) was added to a solution of 9-(1-diethoxyphosphorylmethoxy-3-hydroxyprop-2-oxy)guanine (74 mg, 0.19 mmol) in N,N-dimethylformamide (5 ml) and stirred for 4 hours at 20° C. After evaporation of the solvent, the residue was chromatographed using reverse-phase silica and eluted with water. The correct fractions were evaporated and the residue recrystallised from water-ethanol affording 9-(1-hydroxy-3-phosphonomethoxyprop-2-oxy)guanine (36 mg, 57%) as a white solid, m.p. >300° C.; $\lambda_{max}$ (H$_2$O) 2.53 ($\epsilon$13,100)nm; $\nu_{max}$ (KBr) 3870, 1710, 1650, 1600, 1380, 1160, 1050 and 940 cm$^{-1}$; $\delta_H$ [(CD$_3$)$_2$SO] 2.75–4.25(3H, v. br.s, D$_2$O exchangeable, 3×OH), 3.61(2H, d, J4.7 Hz, CH$_2$OH), 3.62(2H, d, J8.5 Hz, CH$_2$P), 3.76(2H, d, J4.7 Hz, CH$_2$OCH$_2$P), 6.61(2H, br.s, D$_2$O exchangeable, NH$_2$), 7.89(1H, s, H-8), 10.65(1H, br.s, D$_2$O exchangeable, NH); m/z (FAB+veIon) 3.36(MH+, 61%), 358(MNa+, 71%); Found C,31.11; H,4.47; N,20.76%; C$_9$H$_{14}$N$_5$O$_7$P.0.5-H$_2$O requires C,31.40; H,4.39; N,20.37%.

EXAMPLE 17

9-(1-Diethoxyphosphorylmethoxy-3-hydroxyprop-2-oxy)adenine

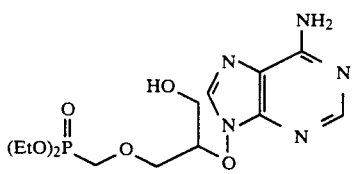

A solution of 9-(1-t-butyldimethylsilyloxy-3-diethoxyphosphorylmethoxyprop-2-oxy)adenine (170 mg, 0.35 mmol) in 80% aqueous acetic acid (5 ml) was stirred at 85° C. for 5 hours. After evaporation, the residue was chromatographed on silica eluting with ethyl acetate-methanol 5:1 affording 9-(1-diethoxyphosphorylmethoxy3-hydroxyprop-2-oxy)adenine (120 mg, 92%) as a clear gum. $\nu_{max}$ (film) 3340; 1700, 1600, 1330, 1290, 1240, 1030 and 970 cm$^{-1}$; $\delta_H$ (CDCl$_3$) 1.38(6H, t, J7.1 Hz, 2×CH$_2$CH$_3$), 3.70(2H, m, CH$_2$OH), 3.89(4H, m, CH$_2$OCH$_2$P), 4.22(4H, m, 2×CH$_2$CH$_3$), 4.50(1H, m, CHON), 5.63(1H, m, D$_2$O exchangeable, OH), 5.89(2H, br.s, D$_2$O exchangeable, NH$_2$), 8.18(1H, s, H-2/H-8), 8.34(1H, s, H-2/H-8); Found: C,39.58; H,5.69; N,17.69%; M+ 375.1317; C$_{13}$H$_{22}$N$_5$O$_6$P.0.9H$_2$O requires C,39.87; H,6.08; N,17.89%; M+ 375.1308.

EXAMPLE 18

9-(1-Hydroxy-3-phosphonomethoxyprop-2-oxy)adenine

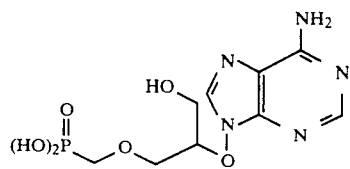

A solution of 9-(1-diethoxyphosphorylmethoxy-3-hydroxyprop-2-oxy)adenine (100 mg, 0.27 mmol) in N,N-dimethylformamide (5 ml) was treated with bromotrimethylsilane (0.36 ml, 2.7 mmol) and stirred for 16 hours at 20° C. After this time, t.l.c. (isopropyl alcohol-water-0.88 ammonia, 60:30:10) showed some monoester still present. More bromotrimethylsilane (0.18 ml, 1.35 mmol) was added and the reaction mixture stirred at 20° C. for 2 hours. The solvent was evaporated and the residual brown oil chromatographed on reverse-phase silica, eluting with water, affording 9-(1-hydroxy-3-phosphonomethoxyprop-2-oxy)adenine (65 mg, 76%) as a white solid; m.p. 222°–225° C.; $\lambda_{max}$ (H$_2$O) 259($\epsilon$12,600)nm; $\nu_{max}$ (KBr) 3420, 1700, 1650, 1620, 1120, and 1060 cm$^{-1}$; $\delta_H$ [(CD$_3$)$_2$SO] 2.7–4.2(3H, v.br.s, D$_2$O exchangeable, 3×OH), 3.64(2H, dJ8.5 Hz, CH$_2$P), 3.67(2H, d, J4.9 Hz, CH$_2$OH), 3.81(2H, d, J4.9 Hz,CH$_2$OCH$_2$P), 4.47(1H, m, $\overline{\text{CHON}}$), 7.43(2H, br.s, D$_2$O exchangeable, NH$_2$), 8.16(1H, s, H 2/H-8), 8.35(1H, s, H-2/H-8); m/z(FAB+veIon) 320(M$^+$, 100%), 342(MNa$^+$, 24%); Found: C,31 77; H,4.67; N.20.83%; C$_9$H$_{14}$N$_5$O$_6$P.1.0H$_2$O requires C,32.05; H,4.78; N,20.77%.

EXAMPLE 19

2,6-Diamino-9-[1-(diethoxyphosphorylmethoxy)-3-hydroxyprop-2-oxy]purine

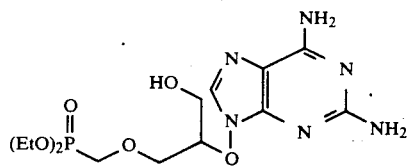

A solution of 6-chloro-9-[1-(diethoxyphosphorylmethoxy)-3-hydroxyprop-2-oxy]-2-formamidopurine (400 mg, 0.91 mmol) in saturated ethanolic ammonia (20 ml) was placed in an autoclave and kept at 110° C. for 5 h. After cooling, the solvent was evaporated in vacuo and the residue chromatographed on silica, eluting with chloroform-methanol 10:1, affording 2,6-diamino-9-[1-(diethoxyphosphorylmethoxy)-3-hydroxyprop-2-oxy]-purine (100 mg, 28%) as an oil. $\nu_{max}$ (CHCl$_3$) 3500, 3400, 1620 and 1600 cm$^{-1}$; $\delta_H$ [(CD$_3$)$_2$SO] 1.24, (6H, t, J7.1 Hz, 2×CH$_2$CH$_3$), 3.58 (2H, m, CH$_2$OH), 3.80 (2H, d, J5.0 Hz, CH$_2$OCH$_2$P), 3.92 (2H, d, $\overline{\text{J}}$8.2 Hz, CH$_2$P), 4.05 (4H,m,2×CH$_2$CH$_3$), 4.39 (1H, t, J5.0 Hz, CHON), 5.35 (1H, br.s, D$_2$O exchangeable, OH), 6.00 (2H br.s, D$_2$O exchangeable, NH$_2$), 6.87 (2H, br.s, D$_2$O exchangeable, NH$_2$), 7.87 (1H, s, H-8); m/z (FAB+ve Ion), 391 (MH$^+$).

EXAMPLE 20

2,6-Diamino-9-1-hydroxy-3-(phosphonomethoxy)prop-2-oxy]purine

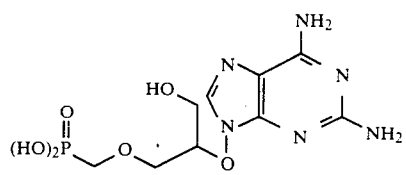

To a solution of 2,6-diamino-9-[1-(diethoxyphosphorylmethoxy)-3-hydroxyprop-2-oxy]purine (100 mg, 0.26 mmol) in dichloromethane, was added bromotrimethylsilane (0.34 ml, 2.6 mmol) and the solution stirred under nitrogen for 4 h at 20° C. The solution was evaporated in vacuo and co-distilled with methanol and toluene. Recrystallisation of the residue with ethanol-water afforded 2,6-diamino-9-[1-hydroxy-3-(phosphonomethoxy)prop-2-oxy]purine (55 mg, 65%) as a white solid m.p. >300° C. decomp. $\lambda_{max}$ (H$_2$O), 280 ($\epsilon$10,100), 255 ($\epsilon$8,400), 212 ($\epsilon$26,100); $\nu_{max}$ (KBr) 3360, 1700, 1660 and 1410 cm$^{-1}$; $\delta_H$ (D$_2$O+NH$_3$) 3.55 (2H, m, CH$_2$OH), 3.89 (4H, m, CH$_2$OCH$_2$P), 4.62 (1H, m, CHON), 8.10 (1H, s, H-8). Found: C, 32.49; H, 4.63; N, 24.86%; C$_9$H$_{15}$N$_6$O$_6$P requires C, 32.34; H, 4.52; N, 25.14%.

EXAMPLE 21

9-[2-Hydroxy-3-(phosphonomethoxy)propoxy]guanine

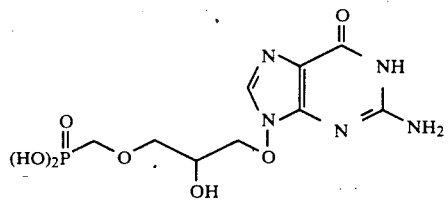

Bromotrimethylsilane (1.43 ml, 10.9 mmol) was added to a solution of 2-amino-9-[3-(diethoxyphosphorylmethoxy)-2-hydroxypropoxy]-6-methoxypurine (220 mg, 0.54 mmol) in dichloromethane (10 ml) and then stirred at 20° C. for 16 h. The reaction mixture was evaporated in vacuo and co-evaporated with toluene. The residue was recrystallised from water-acetone affording 9-[2-hydroxy-3-(phosphonomethoxy)propoxy]-guanine (131 mg, 72%) as a white solid m.p. 245°–247° C., decomp. $\lambda_{max}$ (H$_2$O) 252 ($\epsilon$13,200)nm; $\nu_{max}$ (KBr) 3400, 3300, 1720, 1640, 1590 and 1380 cm$^{-1}$; $\delta_H$ [(CD$_3$)$_2$SO] 3.58 (2H, m, CH$_2$OCH$_2$P), 3.60 (2H, d, J8.5 Hz, CH$_2$P), 3.91 (1H, m, CHOH), 4.17 (1H, m, CH$_2$ON), 4.30 (1H, m, CH$_2$ON), 6.64 (2H, br.s, D$_2$O exchangeable, NH$_2$), 7.93 (1H, s, H-8), 10.63 (1H, br.s, D$_2$O exchangeable, NH); m/z (FAB+ve Ion), 336 (MH$^+$). Found: C, 32.32; H, 4.08; N, 20.66%; C$_9$H$_{14}$N$_5$O$_7$P requires C, 32.25; H, 4.21; N, 20.89%.

EXAMPLE 22

9-[3-(Diethoxyphosphorylmethoxy)-2-hydroxypropoxy]adenine

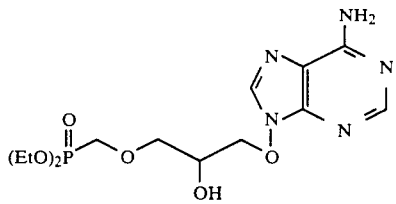

A solution of 9-[2-(t-butyldimethylsilyloxy)-3-(diethoxyphosphorylmethoxy)propoxy]adenine (410 mg, 0.84 mmol) in 80% acetic acid (20 ml) was stirred at 85° C. for 4 h. The solvents were evaporated in vacuo and the residue chromatographed on silica, eluting with chloroform-methanol 10:1, affording 9-[3-(diethoxyphosphorylmethoxy)-2-hydroxypropoxy]adenine (235 mg, 75%) as a white solid m.p. 84°–85° C. $\nu_{max}$ (KBr) 3320, 1650, 1600 and 1460 cm$^{-1}$; $\delta_H$ (CDCl$_3$) 1.33 (6H, t, J6.8 Hz, 2×CH$_3$CH$_2$), 3.75 (2H, d, J5.5 Hz, CH$_2$OCH$_2$P); 3.87 (2H, d, J7.9 Hz, CH$_2$P), 4.06 (1H, m, CHOH), 4.16 (4H, m, 2×CH$_3$CH$_2$), 4,42 (2H, m, CH$_2$ON), 5.60 (1H, br.s, D$_2$O exchangeable, OH), 5.84 (2H, br.s, D$_2$O exchangeable, NH$_2$), 8.01 (1H, s, H-2/H-8), 8.35 (1H, s, H-2/H-8). Found: C, 41.66; H, 5.95; N, 18.55%; M+ 375.1306. C$_{13}$H$_{22}$N$_5$O$_6$P requires C, 41.60; H, 5.91; N, 18.66%; M+ 375.1308.

EXAMPLE 23

9-[2-Hydroxy-3-(phosphonomethoxy)propoxy]adenine

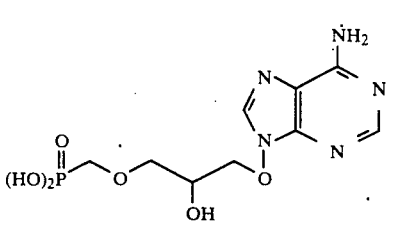

Bromotrimethylsilane (1.4 ml, 10.6 mmol) was added to a solution of 9-[3-(diethoxyphosphorylmethoxy)-2-hydroxypropoxy]adenine (200 mg, 0.52 mmol) in dichloromethane (8 ml) and stirred under nitrogen for 16 h at 20° C. The solvents were evaporated in vacuo, co-evaporating the residue with methanol and toluene. The residue was recrystallised from water-acetone 1:1, affording 9-[2-hydroxy-3-(phosphonomethoxy)propoxy]adenine (130 mg, 76%) as a white solid m.p. 218°–221° C. $\lambda_{max}$ (H$_2$O), 259 ($\epsilon$13,500)nm; $\nu_{max}$ (KBr) 3400, 1700 and 1620 cm$^{-1}$; $\delta_H$ [(CD$_3$)$_2$SO] 3.59 (4H, m, CH$_2$OCH$_2$P), 3.95 (1H, m, CH$_2$OH), 4.27 (1H, m, CH$_2$ON), 4.39 (1H, m, CH$_2$ON), 7.43 (2H, br.s, D$_2$O exchangeable, NH$_2$), 8.16 (1H, s, H-2/H-8), 8.39 (1H, s, H-2/H-8); m/z (FAB+ve Ion), 320 (MH+). Found: C, 33.79; H, 4.79; N, 22.00%; C$_9$H$_{14}$N$_5$O$_6$P requires C, 33.86; H, 4.42; N, 21.94%.

EXAMPLE 24

9-[4-(Diethoxyphosphorylmethoxy)-1-hydroxybut-2-oxy]guanine

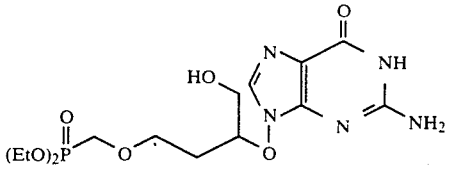

A solution of 2-[bis(t-butoxycarbonyl)amino]-9-[1-(t-butyldimethylsilyloxy)-4-(diethoxyphosphorylmethoxy)but-2-oxy]-6-methoxypurine (415 mg, 0.57 mmol) was dissolved in ethanol (5 ml) and 5M hydrochloric acid (0.6 ml) and heated under reflux for 3.5 h. The reaction was evaporated in vacuo and the residue chromatographed on silica, eluting with chloroform-methanol 10:1, affording 9-[4-(diethoxyphosphorylmethoxy)-1-hydroxybut-2-oxy]guanine (110 mg, 48%) as a pale tan solid. $\nu_{max}$ (KBr) 3400, 1680, 1640 and 1600 cm$^{-1}$; $\delta_H$ [(CD$_3$)$_2$SO] 1.22 (6H, t, J7.1 Hz, 2×CH$_2$CH$_3$), 1.91 (2H, m, CHCH$_2$CH$_2$O), 3.54 (2H, m, CH$_2$OH), 3.74 (2H, m, CH$_2$OCH$_2$P), 3.85 (2H, d, J8.2 Hz, CH$_2$P), 4.03 (4H, m, 2×CH$_2$CH$_3$), 4.30 (1H, m, HOCH$_2$CH), 5.01 (1H, m, D$_2$O exchangeable OH), 6.65 (2H, br.s, D$_2$O exchangeable, NH$_2$); m/z (FAB+ve Ion), 428 (MNa+), 406 (MH+).

EXAMPLE 25

9-[1-Hydroxy-4-(phosphonomethoxy)but-2-oxy]guanine

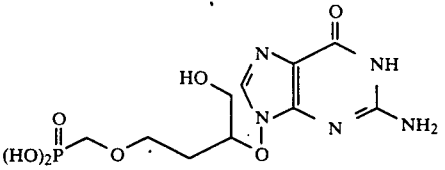

A solution of 9-[4-(diethoxyphosphorylmethoxy)-1-hydroxybut-2-oxy]guanine (95 mg, 0.23 mmol) in N,N-dimethylformamide (5 ml) was treated with bromotrimethylsilane (0.62 ml, 4.6 mmol) and stirred at 20° C. for 3 h. The reaction mixture was evaporated in vacuo, the residue dissolved in water and passed down reverse-phase silica eluting with water. Evaporation of the appropriate fractions in vacuo gave a white foamy solid which was recrystallised from acetone-water, affording 9-[1-hydroxy-4-(phosphonomethoxy)but-2-oxy]guanine (20 mg, 24%) as a white solid m.p. 188°–192° C. $\nu_{max}$ (KBr) 3400, 3100, 1700, 1650 and 1600 cm$^{-1}$; $\delta_H$ [(CD$_3$)$_2$SO] 1.85 (2H, m, HOCH$_2$CHCH$_2$), 3.30 (2H, br.s, D$_2$O exchangeable, P(OH)$_2$), 3.4–3.7 (6H,m, CH$_2$OCH$_2$P+CH$_2$OH), 4.30 (1H, m, HOCH$_2$CH), 5.0 (1H, br.s, D$_2$O exchangeable, OH), 6.62 (2H, br.s, D$_2$O exchangeable, NH$_2$), 7.86 (1H, s, H-8); m/z (FAB+ve Ion), 372 (MNa+), 350 (MH+); Found: C, 33.97; H, 4.69; N, 20.11%; C$_{10}$H$_{16}$N$_5$O$_7$P requires C, 34.29; H, 4.62; N, 20.10%.

EXAMPLE 26

9-[4-(Diethoxyphosphorylmethoxy)-1-hydroxybut-2ox-y]adenine

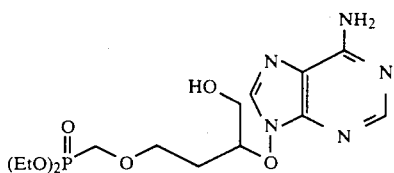

A solution of 9-[1-(t-butyldimethylsilyloxy)-4-(diethoxyphosphorylmethoxy)but-2-oxy]adenine (360 mg, 0.72 mmol) in 80% acetic acid (15 ml) was stirred at 85° C. for 3 h. The solvents were evaporated under vacuum and co-evaporated with toluene. The residue was chromatographed on silica, eluting with chloroform-methanol 10:1, affording 9-[4-(diethoxyphosphorylmethoxy)-1-hydroxybut-2-oxy]adenine (220 mg, 79%) as a white solid, m.p. 86°–88° C. $\nu_{max}$ (KBr) 3350, 3140, 1660, 1600 and 1540 cm$^{-1}$; $\delta_H$(CDCl$_3$) 1.36 (6H, t, J6.8 Hz, 2×C$H_3$CH$_2$), 2.03 (1H, m, HOCH$_2$CHC$H_2$), 2.23 (1H, m, $\overline{\text{H}}$OCH$_2$CHC$H_2$), 3.66 (2H, m, C$H_2$O$\overline{\text{H}}$)), 3.86 (4H, m, C$H_2$OC$H_2$P), $\overline{4}$.21 (4H, m, 2×C$\overline{H}_3$C$H_2$), 4.48 (1H, m, CHON), 5.32 (1H, br.s, D$_2$O exchangeable, OH), 6.02 (2H, br.s, D$_2$O exchangeable NH$_2$), 8.24 (1H, s, H-2/H-8), 8.34 (1H, s, H-2/H-8). Found: C, 43.33; H, 6.27; N, 17.81%; M+ 389.1469. C$_{14}$H$_{24}$N$_5$O$_6$P requires C, 43.19; H, 6.21; N, 17.99%; M+ 389.1464.

EXAMPLE 27

9-1-Hydroxy-4-(phosphonomethoxy)but-2-oxy]adenine

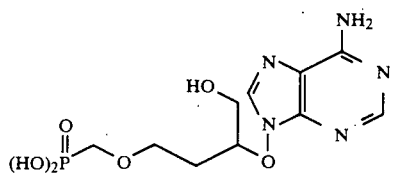

Bromotrimethylsilane (0.71 g, 0.61 ml, 4.6 mmol) was added to a solution of 9-[4-(diethoxyphosphorylmethoxy)-1-hydroxybut-2-oxy]adenine (90 mg, 0.23 mmol) in dichloromethane (5 ml) and the solution stirred for 16 h at 20° C. under nitrogen. The reaction was evaporated in vacuo and co-evaporated with methanol and toluene to give a yellowish residue. The residue was recrystallised from acetone-water 2:1 affording 9-[1-hydroxy-4-(phosphonomethoxy)but-2-oxy]adenine (60 mg, 78%) as a pale yellow solid, m.p. 210°–212° C., $\lambda_{max}$ (H$_2$O), 259 ($\epsilon$13,500)nm; $\nu_{max}$ (KBr) 3440, 1710, 1610 and 1410 cm$^{-1}$; $\delta_H$ [(CD$_3$)$_2$SO] 1.96 (2H, m, HOCH$_2$CHC$H_2$), 3.59 (4H, m, C$H_2$OH+C$H_2$P), 3.76 (2H, m, C$H_2$OCH$_2$P), 4.43 (1$\overline{\text{H}}$, m, CHON), 7.54 (2H, br.s, D$_2$O exchangeable, NH$_2$), 8.18 (1H, s, H-2/H-8), 8.39 (1H, s, H-2/H-8); Found: C, 35.12; H, 4.91; N, 20.42% C$_{10}$H$_{16}$N$_5$O$_6$P.0.5H$_2$O requires C, 35.09; H, 5.00; N, 20.46%.

Antiviral Activity

1. CPE Inhibition Test (Established Monolayer) for Lentiviruses

3×10$^4$ sheep choroid plexus (SCP) cells were plated into individual wells of a 96 well microtitre plate in 100 μl of Eagle's MEM with Hanks' salts containing 10% heat-inactivated foetal calf serum (FCS). When monolayers had become established (after 1 or 2 days growth) they were washed with 200 μl of maintenance medium (Eagle's MEM with Hanks' salts containing 0.5% FCS) and infected with 100 μl of visna virus (strain K184) in maintenance medium (30 TCID$_{50}$/ml). Test samples were diluted with maintenance medium in further 96 well microtitre plates over the range 200–0.06 μg/ml by 3-fold dilution steps. 100 μl of the diluted samples was then transferred directly onto virus-infected monolayers (final concentration range therefore 100–0.03 μg/ml) and incubated at 37° C. in a humidified atmosphere containing 5% CO$_2$ until virus-induced CPE was maximal in the untreated virus-infected controls (usually 12–14 days). The plates were fixed with formol saline and stained with crystal violet. Virus-induced CPE was then scored microscopically and the minimum concentration of sample giving complete protection of the cell monolayers (MIC) determined.

2. Plaque Reduction Test for Varicella Zoster Virus

MRC-5 cells were grown to confluence in 24 well multi-dishes (well diameter=1.5 cm). The drained cell monolayers were each infected with approximately 50 infectious particles of varicella zoster virus (VZV; Ellen strain) in 100 μl of phosphate-buffered saline. The virus was adsorbed for 1 hour at room temperature. After adsorption, residual inoculum was removed from each well and replaced with 0.5 ml of Eagle's MEM containing 5% heat-inactivated foetal calf serum and 0.9% agarose (A37). Once the agarose had set, dilutions of the test compound, which had been prepared in Eagle's MEM (containing 5% heat-inactivated foetal calf serum), were added, each well receiving 0.5 ml of liquid overlay. The test compound was diluted to give the following series of concentrations: 200, 60, 20, 6 . . . 0.06 μg/ml; final concentrations in the assay ranged, therefore, between 100 μg/ml and 0.03 μg/ml. The infected cultures were incubated at 37° C. in a humidified atmosphere of 5% CO$_2$ until plaques were clearly visible (5 or 6 days).

Cultures from 1 and 2 were fixed in formol saline, the agarose overlays were carefully washed off, and then the cell monolayers were stained with carbol fuchsin. A stereo microscope was used to count plaques. The IC$_{50}$ (concentration of drug which inhibits the number of plaques formed by 50% relative to the number of plaques observed in virus control monolayers) of the test compound was calculated. In addition, the monolayers were examined for evidence of drug-induced cytotoxicity; the minimum concentration at which cytotoxicity occurs was recorded.

3. Plaque Reduction Test for Cytomegalovirus

MRC-5 cells were grown to confluence in 24 well multi-dishes (well diameter=1.5 cm). The drained cell monolayers were each infected with approximately 50 infectious particles of cytomegalovirus (CMV; AD-169 strain) in 100 μl of phosphate-buffered saline. The virus was adsorbed for 1 hour at room temperature. After adsorption, residual inoculum was removed from each well and replaced with 1 ml of Eagle's MEM containing 10% heat-inactivated foetal calf serum and 0.9% agarose (A37). Once the agarose had set, dilutions of the test compound, which had been prepared in Eagle's MEM (containing 10% heat-inactivated calf serum), were added, each well receiving 1 ml of liquid overlay. The test compound was diluted to give the following series of concentrations: 200, 60, 20, 6 ... 0.06 μg/ml; final concentrations in the assay range, therefore, between 100 μg/ml and 0.03 μg/ml. The infected cultures were incubated at 37° C. in a humidified atmosphere containing 5% $CO_2$ until plaques were clearly visible (about 12 days). The cultures are fixed in formol saline, the agarose overlays were carefully washed off, and then the cell monolayers were stained with carbol fuchsin. A stereo microscope was used to count plaques. The $IC_{50}$ (concentration of drug which inhibits the number of plaques formed by 50% relative to the number of plaques observed in virus control monolayers) of the test compound was calculated. In addition, the monolayers were examined for evidence of drug-induced cytotoxicity; the minimum concentration at which cytotoxicity occurs was recorded.

Results

The compounds of Examples 2, 7 and 16 were active against visna virus with $IC_{50}$ values of 1.0, 3 and 10 μg/ml respectively.

The compound of Example 16 was also active against varicella-zoster virus ($IC_{50}$ 6.2 μg/ml) and cytomegalovirus ($IC_{50}$ 4.4 μg/ml).

Toxicity

The compounds were not toxic for the cell monolayers at concentrations up to 100 μg/ml.

We claim:

1. A compound of formula (I), or a pharmaceutically acceptable salt thereof:

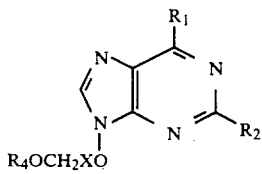

(I)

wherein $R_1$ is hydroxy, amino, chloro or $OR_7$ wherein $R_7$ is $C_{1-6}$ alkyl, phenyl $C_{1-2}$ alkyl either of which phenyl moieties may be substituted by one or two substituents selected from halo, $C_{1-4}$ alkyl or $C_{1-4}$ alkoxy;

$R_2$ is amino or, when $R_1$ is hydroxy or amino, $R_2$ may also be hydrogen;

X is —$CH_2CH_2$— or a moiety of structure (a), (b) or (c):

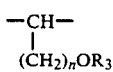 (a)

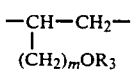 (b)

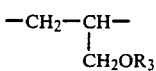 (c)

wherein n is 1 or 2;

m is 0, 1 or 2; and $R_3$ is hydrogen or $C_{1-7}$ alkanoyl or benzoyl optionally substituted in the phenyl ring by one, two or three groups or atoms selected from halogen, $C_{1-4}$ alkyl and $C_{1-4}$ alkoxy;

$R_4$ is a group of formula:

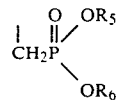

wherein $R_5$ and $R_6$ are independently selected from hydrogen, $C_{1-6}$ alkyl and phenyl or phenyl substituted by one, two or three groups or atoms selected from halogen, $C_{1-4}$ alkyl and $C_{1-4}$ alkoxy.

2. A compound according to claim 1 wherein $R_1$ is hydroxy and $R_2$ is amino, or $R_1$ is amino and $R_2$ is hydrogen.

3. A compound according to claim 1 wherein X is —$CH_2CH_2$—.

4. A compound according to claim 1 wherein X is of structure (a) as defined in claim 1, and n is 1.

5. A compound according to claim 1 wherein $R_5$ and $R_6$ are both hydrogen.

6. A compound selected from the group consisting of:
9-[3-(diethoxyphosphorylmethoxy)propoxy]guanine,
9-[3-(phosphonomethoxy)propoxy]guanine,
2,6-diamino-9-[3-(diethoxyphosphorylmethoxy)-propoxy]purine,
2,6-diamino-9-[3-(phosphonomethoxy)propoxy]purine,
9-[3-(diethoxyphosphorylmethoxy)propoxy]adenine,
9-[3-(phosphonomethoxy)propoxy]adenine,
9-[3-(ethoxy(hydroxy)phosphorylmethoxy)propoxy]-guanine,
2,6-diamino-9-[(3-diethoxyphosphorylmethoxy-2-hydroxymethyl)propoxy]purine,
2,6-diamino-9-[(2-hydroxymethyl-3-phosphonomethoxy)propoxy]purine,
9-[(3-diethoxyphosphorylmethoxy-2-hydroxymethyl)propoxy]guanine,
9-[(2-hydroxymethyl-3-phosphonomethoxy)propoxy]guanine,
9-[(3-diethoxyphosphorylmethoxy-2-hydroxymethyl)propoxy]adenine,
9-[(2-hydroxymethyl-3-phosphonomethoxy)propoxy]adenine,
9-[(3-ethoxy(hydroxy)phosphorylmethoxy-2-hydroxymethyl)propoxy]guanine,
9-(1-diethoxyphosphorylmethoxy-3-hydroxyprop-2-oxy)guanine,
9-(1-hydroxy-3-phosphonomethoxyprop-2-oxy)guanine,
9-(1-diethoxyphosphorylmethoxy-3-hydroxyprop-2-oxy)adenine,
9-(1-hydroxy-3-phosphonomethoxyprop-2-oxy)adenine,
2,6-diamino-9-[1-(diethoxyphosphorylmethoxy)-3-hydroxyprop-2-oxy]purine,
2,6-diamino-9-[1-hydroxy-3-(phosphonomethoxy)-prop-2-oxy]purine,
9-[2-hydroxy-3-(phosphonomethoxy)propoxy]guanine,
9-[3-(diethoxyphosphorylmethoxy)-2-hydroxypropoxy]adenine,
9-[2-hydroxy-3-(phosphonomethoxy)propoxy]adenine, 9-[4-(diethoxyphosphorylmethoxy)-1-hydroxybut-2-oxy]guanine, 9-[1-hydroxy-4-(phosphonomethoxy)but-2-oxy]guanine, 9-[4-(diethoxyphosphorylmethoxy)-1-hydroxybut-2-oxy]adenine and 9-[1-hydroxy-4-(phosphonomethoxy)but-2-oxy]adenine.

7. A pharmaceutical composition for use in treating viral infections caused by viruses selected from the group consisting of lentiviruses, varicella-zoster virus, and cytomegalovirus comprising an effective amount of a compound according to claim 1 and a pharmaceutically acceptable carrier.

8. A method of treatment of viral infections caused by viruses selected from the group consisting of lentiviruses, varicella-zoster virus, and cytomegalovirus in mammals, which comprises the administration to the mammal in need of such treatment, an effective amount of a compound according to claim 1.

9. The compound 9-(1-Hydroxy-3-phosphonomethoxyprop-2-oxy)guanine.

10. A method of treatment of cytomegalovirus infections in mammals comprising the administration to a mammal of an effective amount of the compound according to claim 9.

* * * * *